(12) United States Patent
Iguchi

(10) Patent No.: US 11,493,747 B2
(45) Date of Patent: Nov. 8, 2022

(54) OPTICAL UNIT AND ENDOSCOPE

(71) Applicant: OLYMPUS CORPORATION, Tokyo (JP)

(72) Inventor: Takehiko Iguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 39 days.

(21) Appl. No.: 17/125,153

(22) Filed: Dec. 17, 2020

(65) Prior Publication Data

US 2021/0103136 A1 Apr. 8, 2021

Related U.S. Application Data

(63) Continuation of application No. PCT/JP2018/026316, filed on Jul. 12, 2018.

(51) Int. Cl.
*G02B 23/24* (2006.01)
*A61B 1/00* (2006.01)

(52) U.S. Cl.
CPC ....... *G02B 23/243* (2013.01); *G02B 23/2461* (2013.01); *G02B 23/2476* (2013.01); *A61B 1/0019* (2013.01)

(58) Field of Classification Search
CPC .............. G02B 23/243; G02B 23/2461; G02B 23/2476; A61B 1/0019
See application file for complete search history.

(56) References Cited

U.S. PATENT DOCUMENTS

| | | | |
|---|---|---|---|
| 2016/0341950 A1 | 11/2016 | Kono et al. | |
| 2017/0065157 A1 | 3/2017 | Iwasaki et al. | |
| 2018/0049621 A1 | 2/2018 | Iguchi et al. | |
| 2021/0181456 A1* | 6/2021 | Hagiwara | ............... G03B 17/12 |

FOREIGN PATENT DOCUMENTS

| | | | |
|---|---|---|---|
| EP | 3 104 206 A1 | 12/2016 | |
| EP | 3 133 431 A1 | 2/2017 | |
| JP | 2010-243195 A | 10/2010 | |
| JP | 2015-148704 A | 8/2015 | |
| WO | 2015/118711 A1 | 8/2015 | |
| WO | 2015/178126 A1 | 11/2015 | |
| WO | 2016/166857 A1 | 10/2016 | |
| WO | WO 2016166857 | * 10/2016 | ........... A61B 1/0019 |

OTHER PUBLICATIONS

International Search Report dated Sep. 11, 2018 received in PCT/JP2018/026316.

* cited by examiner

*Primary Examiner* — James T Boylan
(74) *Attorney, Agent, or Firm* — Scully, Scott, Murphy & Presser, P.C.

(57) ABSTRACT

An optical unit includes a movable section that holds a movable lens group and includes a rotation restricting section, a fixed section that holds a fixed lens group and has specific permeability larger than 1.0, n thinned-down sections being provided in the fixed section, and a voice coil motor including an n magnet sections disposed at every (360/n)° around a center axis of the movable section and a coil section disposed in the fixed section. The n magnet sections are respectively housed in n thinned-down sections in a noncontact manner. The n thinned-down sections are formed in asymmetrical positions different from every (360/n)° around the center axis.

9 Claims, 32 Drawing Sheets

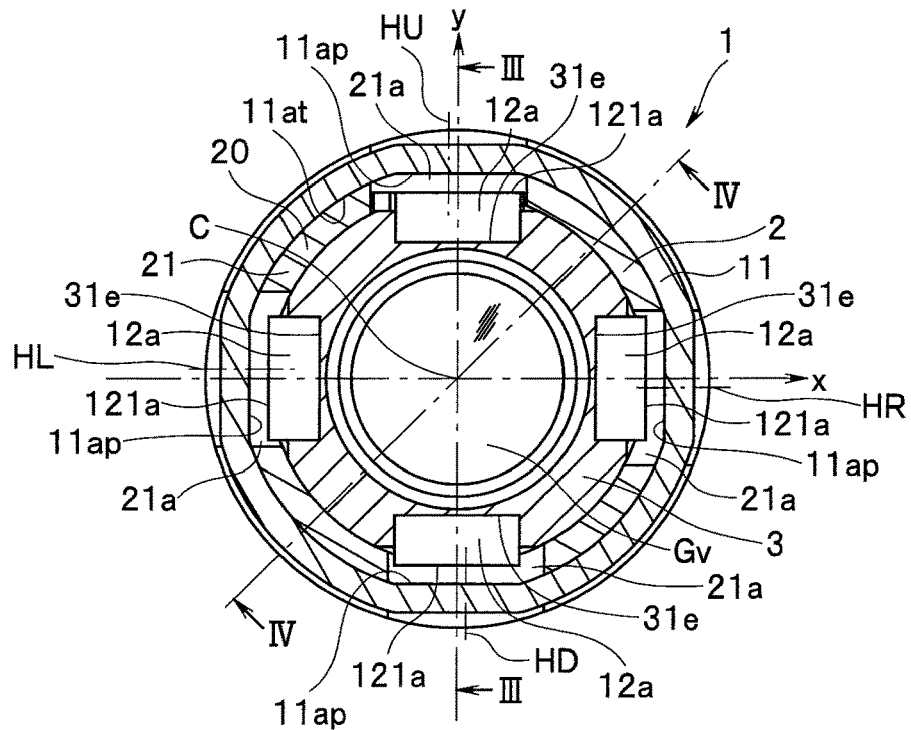

US 11,493,747 B2

OPTICAL UNIT AND ENDOSCOPE

CROSS REFERENCE TO RELATED APPLICATION

This application is a continuation application of PCT/JP2018/026316 filed on Jul. 12, 2018, the entire contents of which are incorporated herein by this reference.

BACKGROUND OF THE INVENTION

1. Field of the Invention

The present invention relates to an optical unit that drives a movable section to advance and retract using a voice coil motor and relates to an endoscope including an optical unit.

2. Description of the Related Art

There has been disclosed an endoscope including a movable lens frame to which a lens is attached and including a zoom function for changing photographing magnification by moving the movable lens frame to advance and retract.

An example of such an endoscope is described in Japanese Patent Application Laid-Open Publication No. 2010-243195.

SUMMARY OF THE INVENTION

An optical unit according to an aspect of the present invention includes: a movable section formed in a tubular shape for holding a movable lens group on an inner side; a fixed section formed in a tubular shape for holding, on an inner side, at least one of an object-side fixed lens group disposed further on an object side than the movable lens group and an image-side fixed lens group disposed further on an image side than the movable lens group, the fixed section being disposed on an outer side of the movable section to have a center axis common to the movable section; and a voice coil motor including n magnet sections disposed in the movable section, where n is an integer equal to or larger than 2, and a coil section disposed in the fixed section, the voice coil motor being able to move the movable section in a direction of the center axis relatively to the fixed section by applying an electric current to the coil section. The n magnet sections are each magnetically polarized in a direction crossing the center axis and disposed at every $(360/n)°$ in symmetrical positions around the center axis in the movable section. The fixed section is formed in the tubular shape using a material having specific permeability larger than 1.0, n thinned-down sections for respectively housing the n magnet sections in a noncontact manner being provided in the fixed section. The movable section includes a rotation restricting section disposed on an inside of at least one thinned-down section among the n thinned-down sections, and the rotation restricting section engages with the thinned-down section and restricts rotation of the movable section around the center axis to thereby maintain a state in which the n magnet sections are in noncontact with the fixed section. The n thinned-down sections are formed in asymmetrical positions around the center axis and includes at least one pair of two thinned-down sections adjacent to each other around the center axis, an angle around the center axis of centers of the pair of thinned-down sections being different from the $(360/n)°$.

An endoscope according to an aspect of the present invention is an endoscope that is inserted into an inside of a subject and observes the inside of the subject, the endoscope including: the optical unit; and an image pickup device configured to convert light condensed by the optical unit into an electric signal.

BRIEF DESCRIPTION OF THE DRAWINGS

FIG. 2 is a sectional view of the optical unit when viewed on a cut surface passing a I-I line of FIG. 4 in the first embodiment;

FIG. 3 is a sectional view of the optical unit when viewed on a cut surface passing a II-II line of FIG. 4 in the first embodiment;

DETAILED DESCRIPTION OF THE PREFERRED EMBODIMENTS

Embodiments of the present invention are explained below with reference to the drawings.

First Embodiment

FIG. 1 to FIG. 18 show a first embodiment of the present invention.

Figure 1:
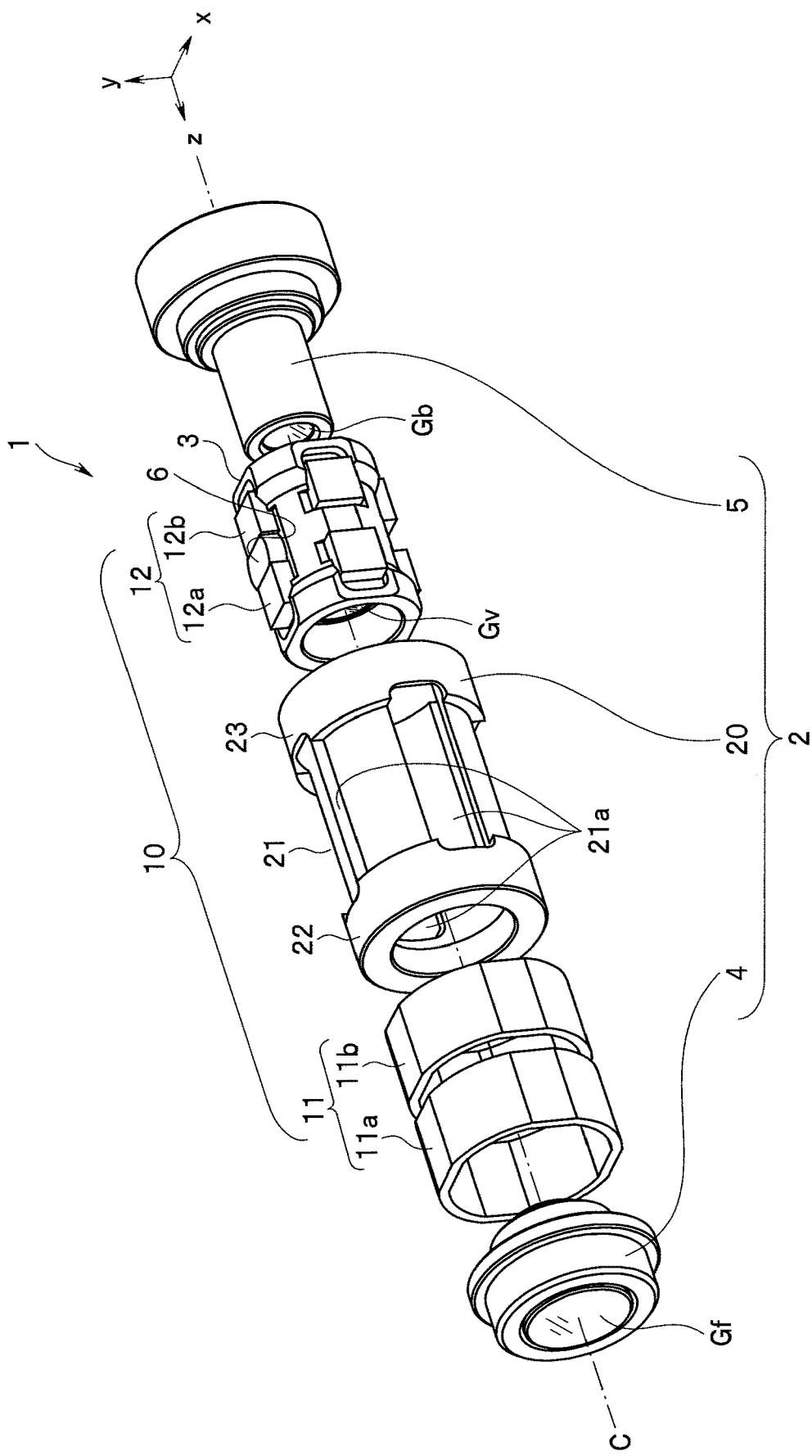
FIG. 1 is an exploded perspective view showing a configuration of an optical unit according to a first embodiment of the present invention.
Figure 4:
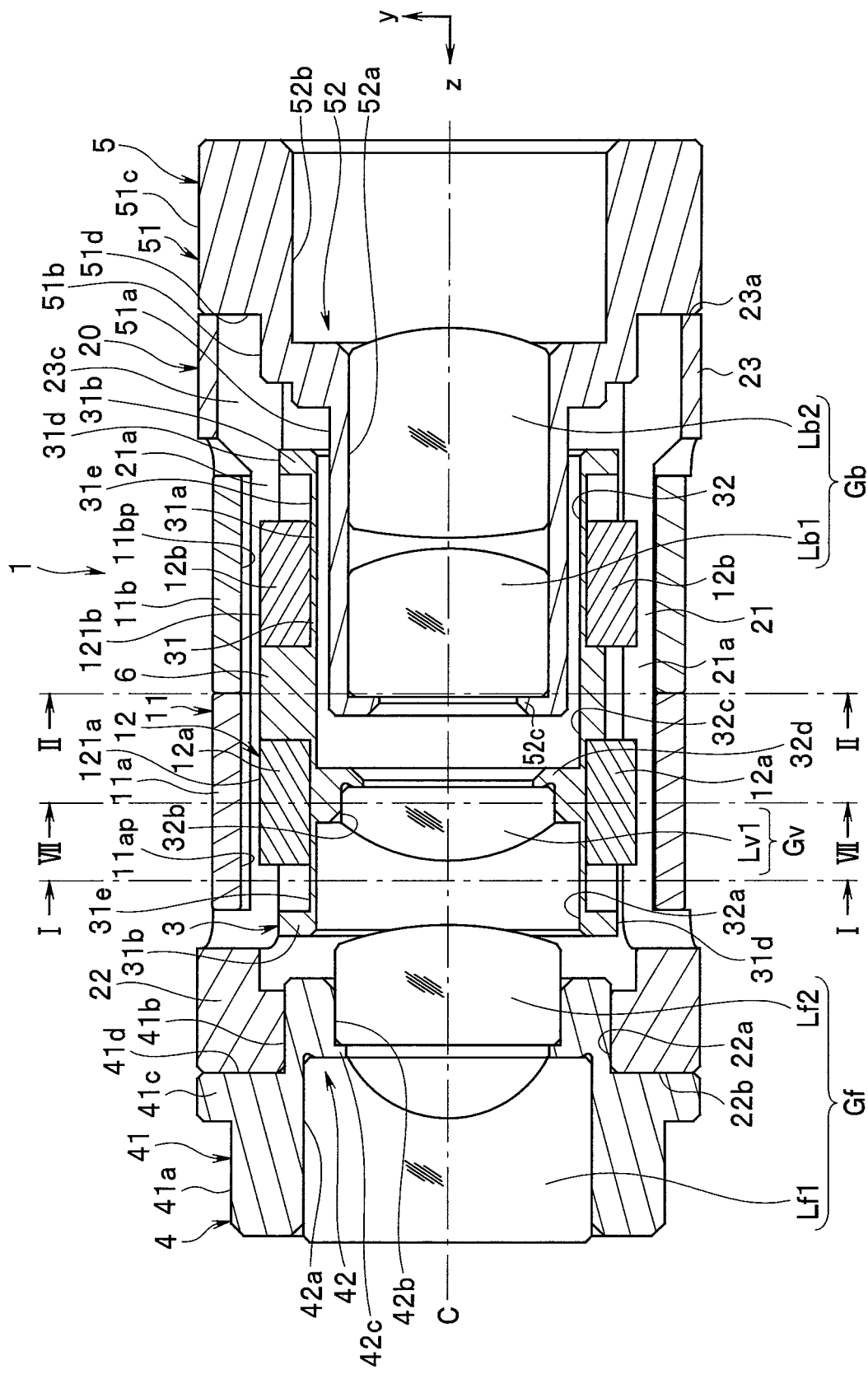
FIG. 4 is a sectional view of the optical unit when viewed on a cut surface passing a line of FIG. 2 in the first embodiment.
Figure 5:
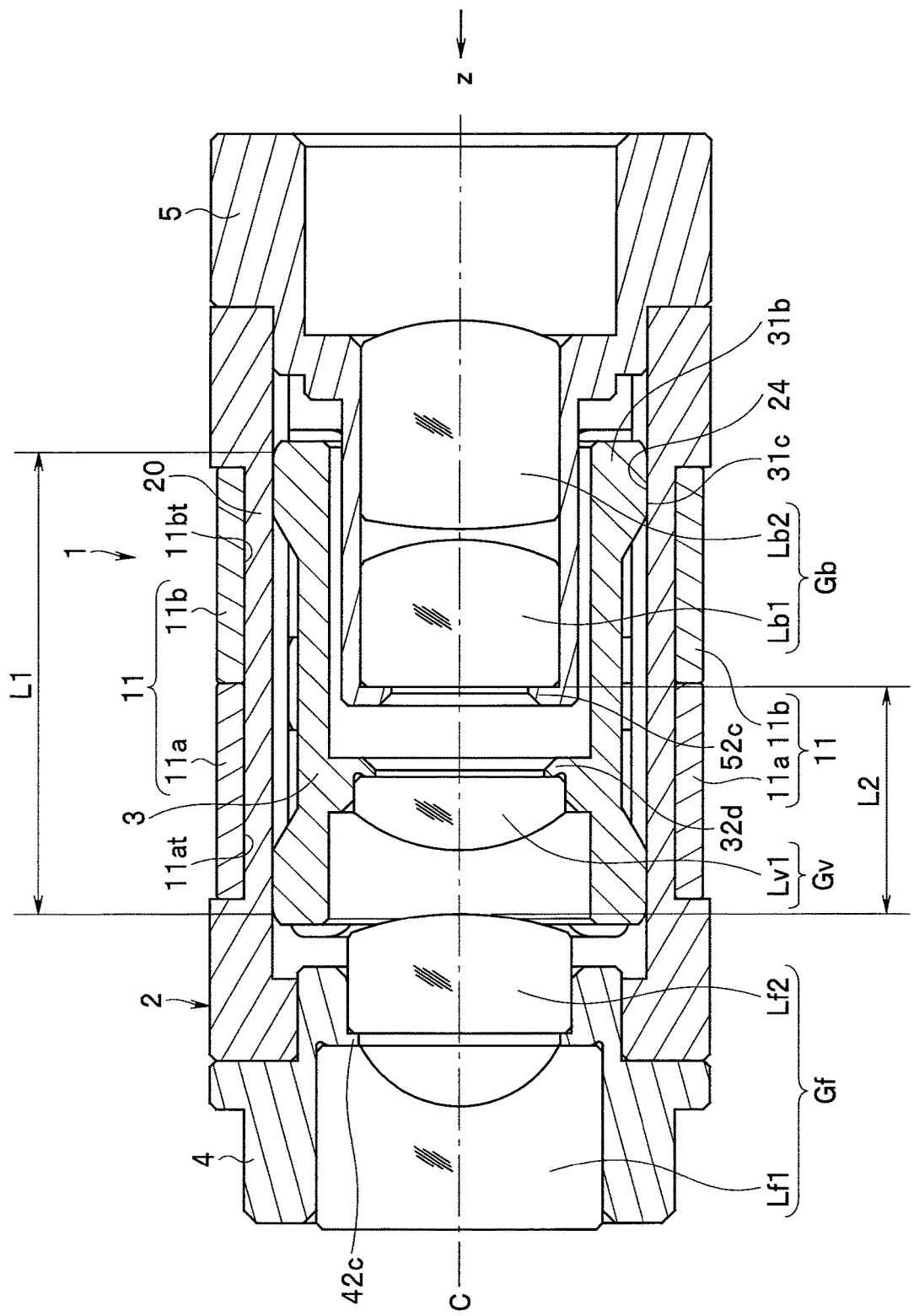
FIG. 5 is a sectional view of the optical unit when viewed on a cut surface passing a IV-IV line of FIG. 2 in the first embodiment.

FIG. 1 is an exploded perspective view showing a configuration of an optical unit 1 according to a first embodiment of the present invention. FIG. 2 is a sectional view of the optical unit 1 when viewed on a cut surface passing a I-I line of FIG. 4 in the first embodiment. FIG. 3 is a sectional view of the optical unit 1 when viewed on a cut surface passing a II-II line of FIG. 4 in the first embodiment. FIG. 4 is a sectional view of the optical unit 1 when viewed on a cut surface passing a III-III line of FIG. 2 in the first embodiment. FIG. 5 is a sectional view of the optical unit 1 when viewed on a cut surface passing a IV-IV line of FIG. 2 in the first embodiment.

The optical unit 1 shown in FIG. 1 to FIG. 5 includes a fixed section 2, a movable section 3 movable with respect to the fixed section 2, and a voice coil motor 10 that generates a driving force for moving the movable section 3 with respect to the fixed section 2.

The movable section 3 is formed in a tubular shape and holds a movable lens group Gv on an inner side.

The fixed section 2 is formed in a tubular shape and holds at least one of an object-side fixed lens group Gf or an image-side fixed lens group Gb on an inner side. In particular, the fixed section 2 in the embodiment holds both of the object-side fixed lens group Gf and the image-side fixed lens group Gb on the inner side. The fixed section 2 is disposed on an outer side of the movable section 3 to have an axis C, which is a center axis common to the movable section 3.

More specifically, the fixed section 2 includes a fixed section main body 20, a front frame section 4 attached to an object side of the fixed section main body 20, and a rear frame section 5 attached to an image side of the fixed section main body 20. The front frame section 4 holds the object-side fixed lens group Gf. The rear frame section 5 holds the image-side fixed lens group Gb.

The object-side fixed lens group Gf is disposed further on the object side than the movable lens group Gv. The image-side fixed lens group Gb is disposed further on the image side than the movable lens group Gv. The object-side fixed lens group Gf, the movable lens group Gv, and the image-side fixed lens group Gb configure an imaging optical system that forms, as an image, light made incident from an object.

Figure 6:
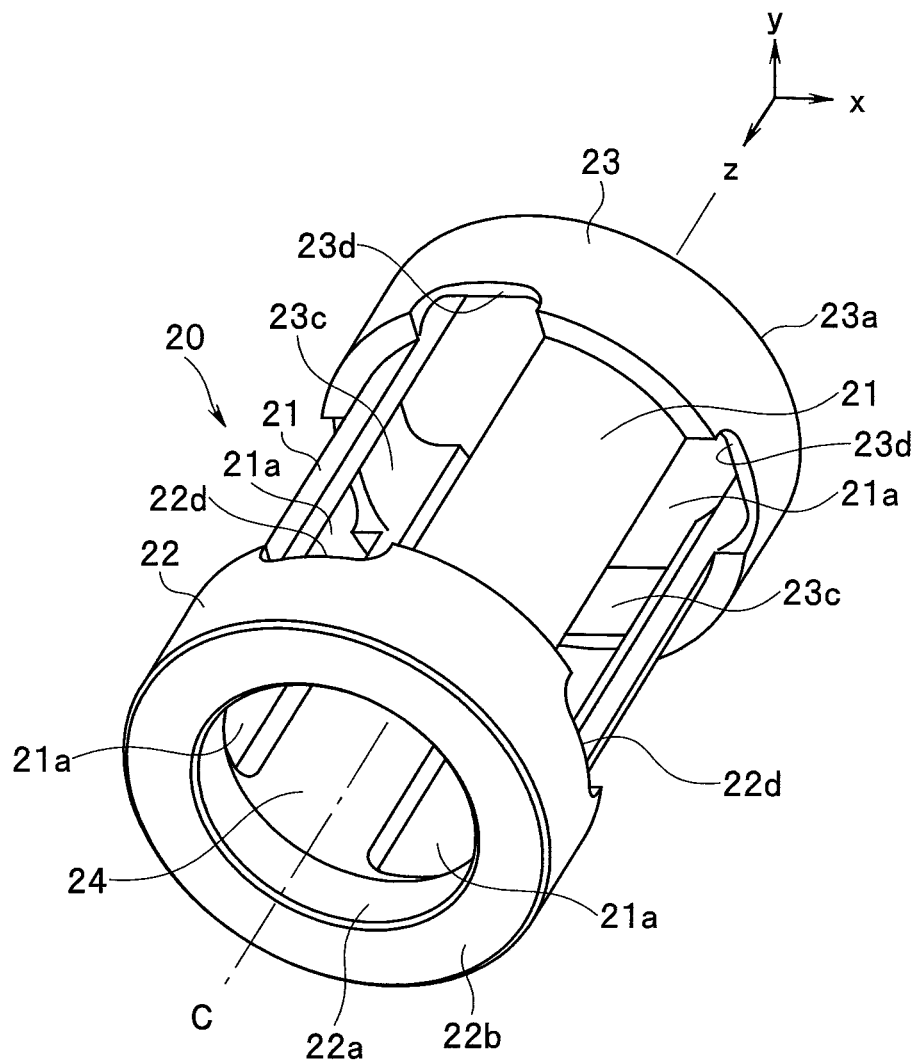
FIG. 6 is a perspective view showing a configuration of a fixed section main body of the optical unit according to the first embodiment.
Figure 7:
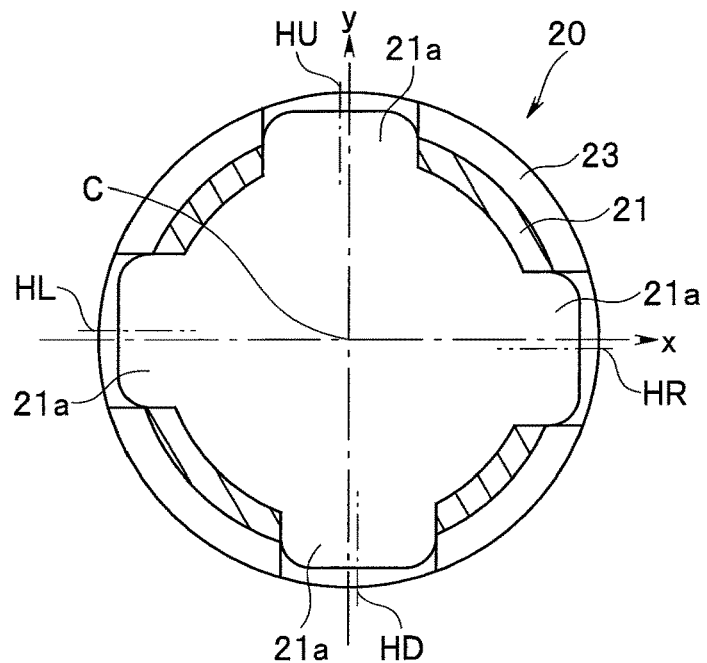
FIG. 7 is a sectional view of the fixed section main body when viewed on a cut surface passing a V-V line of FIG. 8 in the first embodiment.
Figure 8:
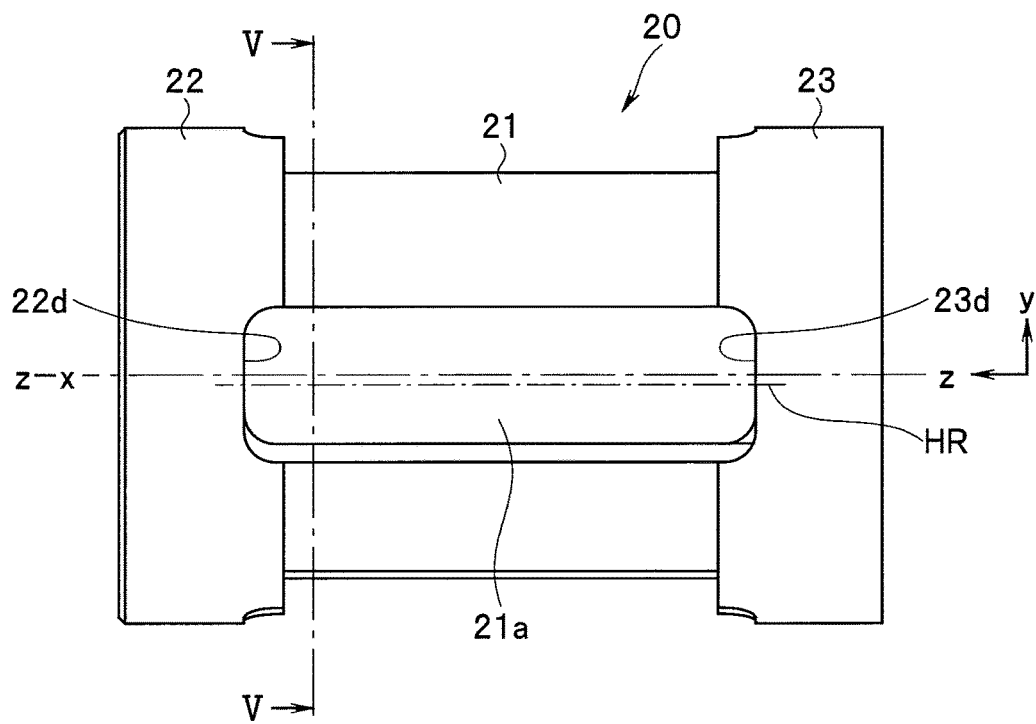
FIG. 8 is a side view showing the configuration of the fixed section main body of the optical unit according to the first embodiment.

FIG. 6 is a perspective view showing a configuration of the fixed section main body 20 of the optical unit 1. FIG. 7 is a sectional view of the fixed section main body 20 when viewed on a cut surface passing a V-V line of FIG. 8. FIG. 8 is a side view showing the configuration of the fixed section main body 20 of the optical unit 1.

The fixed section main body 20 shown in FIG. 6 to FIG. 8 is configured as a tubular member centering on a predetermined axis C. The axis C is formed to coincide with an optical axis of the imaging optical system (however, when a special optical system is adopted, the axis C is not limited to this).

In the following explanation, an opposite side of the object side in the axis C direction is referred to as image side.

In the respective figures, an object-side direction of the axis C is described as z direction, one direction on a plane perpendicular to the axis C is described as x direction, and a direction perpendicular to the x direction on the plane perpendicular to the axis C is described as y direction to indicate a direction relating to the optical unit 1 in the respective drawings.

The fixed section main body 20 includes a tube section 21 having the axis C as a center axis, a short tubular object-side thick section 22 formed on the object side in the axis C direction with respect to the tube section 21, and a short tubular image-side thick section 23 formed on an opposite side in the axis C direction of the object-side thick section 22 with respect to the tube section 21.

In the tube section 21, thinned-down sections 21a for housing magnet sections 12 explained below in a noncontact manner are formed. In order to house the magnet sections 12 in the noncontact manner, length in the axis C direction of the thinned-down sections 21a is formed larger than length of regions where the magnet sections 12 advance and retract in the axis C direction. Further, in order to house the magnet sections 12 in the noncontact manner, width around the axis C of the thinned-down sections 21a is formed slightly larger than width around the axis C of a rotation restricting section 6 explained below.

More specifically, four thinned-down sections 21a are formed at approximately every 90° along a periphery of the axis C, which is a center axis in a longitudinal direction of the tube section 21. More accurately, some of the four thinned-down sections 21a are disposed to be shifted from positions of every 90° along a circumferential direction. The disposition is explained in detail below.

The thinned-down sections 21a in the embodiment are formed as long holes in the axis C direction that pierce through the tube section 21 in a radial direction of the tube section 21. As shown in FIG. 6, end portions on the object side of the thinned-down sections 21a reach the object-side thick section 22 and configure U-shaped cutout sections 22d and end portions on the image side of the thinned-down sections 21a reach the image-side thick section 23 and configure U-shaped cutout sections 23d.

Note that the thinned-down sections 21a are provided to pierce through the tube section 21. However, the thinned-down sections 21a are not limited to this and may be thinned-down sections that do not pierce through the tube section 21 to a radial direction outer circumference side if the magnet sections 12 and the rotation restricting section 6 explained below can move in parallel to the axis C. In this case, the thinned-down sections are formed in a bottomed groove shape and are configured such that bottom surfaces of grooves are located further on an outer diameter side than surfaces on the outer diameter side of the magnet sections 12 centering on the axis C.

A surface on a radial direction inner side of the tube section 21 excluding the thinned-down sections 21a is a tubular cylindrical surface and is formed as a fixed-side sliding surface 24 that supports and guides the movable section 3. The fixed-side sliding surface 24 is formed in a shape divided in the circumferential direction by the thinned-down sections 21a.

The object-side thick section 22 is formed to project further to a radial direction outer side and the radial direction inner side than the tube section 21. The image-side thick section 23 is formed to project further to the radial direction outer side than the tube section 21. A groove 23c is formed on the fixed-side sliding surface 24 on the radial direction inner side of the image-side thick section 23. When the movable section 3 is assembled, the magnet section 12 and the rotation restricting section 6 explained below pass this groove 23c. Therefore, it is possible to easily assemble the movable section 3 to the fixed section main body 20. Note that the object-side thick section 22 and the image-side thick section 23 may be formed separately from the tube section 21 and attached to the tube section 21 during assembly.

A coil section 11 configuring the voice coil motor 10 is fixed and disposed on an outer circumference side of the tube section 21. As shown in FIG. 1, FIG. 4, and the like, the coil section 11 includes a first coil 11a disposed on the object side in the axis C direction and a second coil 11b disposed on the image side in the axis C direction.

Figure 9:
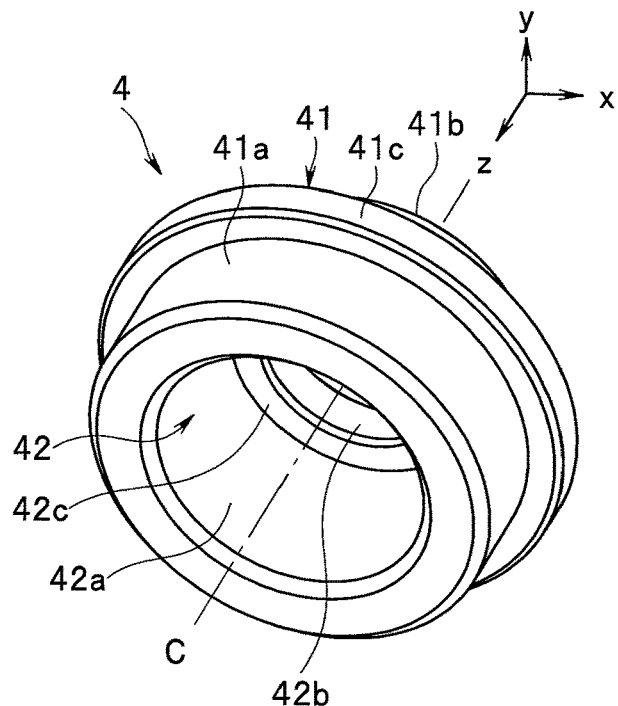
FIG. 9 is a perspective view showing, from an object side, a configuration of a front frame section of the optical unit according to the first embodiment.
Figure 10:
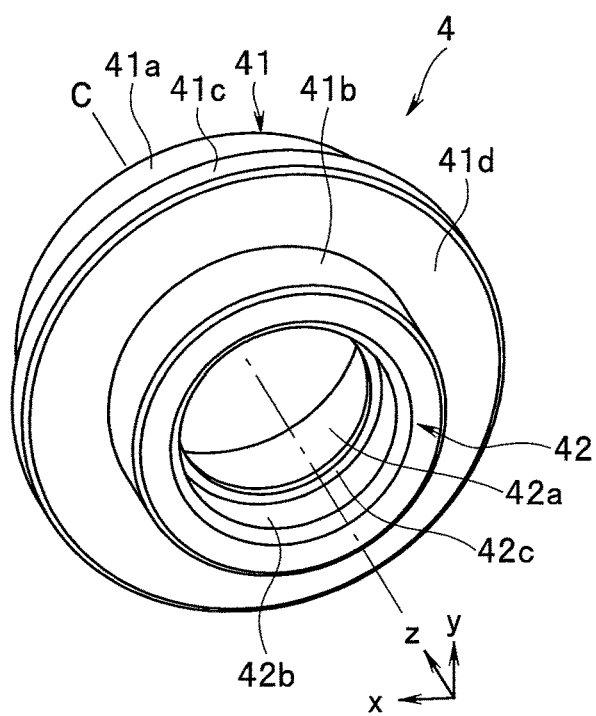
FIG. 10 is a perspective view showing, from an image side, the configuration of the front frame section of the optical unit according to the first embodiment.

FIG. 9 is a perspective view showing, from the object side, a configuration of the front frame section 4 of the optical unit 1. FIG. 10 is a perspective view showing, from the image side, the configuration of the front frame section 4 of the optical unit 1. Note that a center axis of the front frame section 4 is referred to as the axis C because, when the front frame section 4 is assembled to the fixed section main body 20, the center axis of the front frame section 4 coincides with a center axis of the fixed section main body 20.

The front frame section 4 is a tubular member including an outer circumferential section 41 and an inner circumferential section 42. The outer circumferential section 41 includes a first outer circumferential section 41a, a second outer circumferential section 41b, and an outer circumference side convex section 41c. The inner circumferential section 42 includes a first inner circumferential section 42a, a second inner circumferential section 42b, and an inner circumference side convex section 42c.

In the outer circumferential section 41, the first outer circumferential section 41a is larger in diameter than the second outer circumferential section 41b. The outer circumference side convex section 41c having the largest diameter projecting to the radial direction outer side is provided between the first outer circumferential section 41a and the second outer circumferential section 41b.

In the inner circumferential section 42, the first inner circumferential section 42a is larger in diameter than the second inner circumferential section 42b. The inner circumference side convex section 42c having the smallest diameter projecting to the radial direction inner side is located between the first inner circumferential section 42a and the second inner circumferential section 42b.

The front frame section 4 holds the object-side fixed lens group Gf. The object-side fixed lens group Gf includes a front first lens Lf1 and a front second lens Lf2, which are arranged in this order from the object side. The first inner circumferential section 42a holds the front first lens Lf1 and the second inner circumferential section 42b holds the front second lens Lf2. It is preferable that, as shown in FIG. 4 and FIG. 5, the image side of the front first lens Lf1 and the object side of the front second lens Lf2 be in contact with the inner circumference side convex section 42c.

When the front frame section 4 is inserted into the fixed section main body 20, the second outer circumferential section 41b is brought into contact with an inner circumferential surface 22a of the object-side thick section 22 of the fixed section main body 20 and, at the same time, the front frame section 4 is inserted until an end face 22b on the object side of the fixed section main body 20 comes into contact with a step section 41d between the second outer circumferential section 41b and the outer circumference side convex section 41c.

Figure 11:
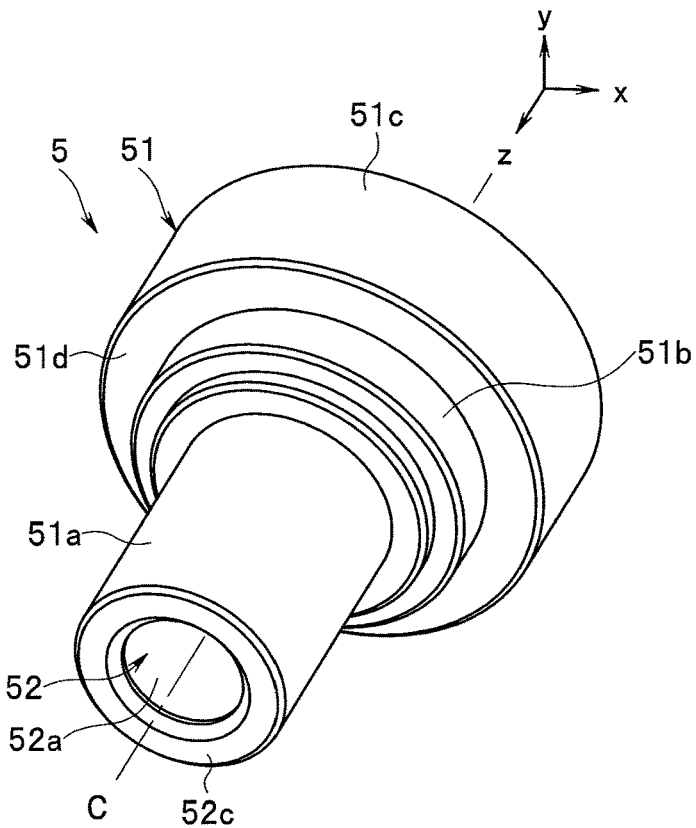
FIG. 11 is a perspective view showing, from the object side, a configuration of a rear frame section of the optical unit according to the first embodiment.
Figure 12:
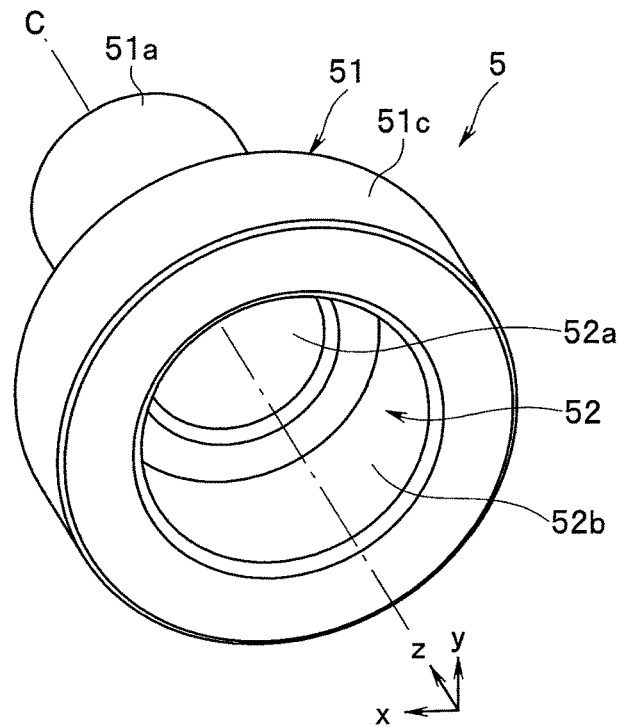
FIG. 12 is a perspective view showing, from the image side, the configuration of the rear frame section of the optical unit according to the first embodiment.

FIG. 11 is a perspective view showing, from the object side, a configuration of the rear frame section 5 of the optical unit 1. FIG. 12 is a perspective view showing, from the image side, the configuration of the rear frame section 5 of the optical unit 1. Note that a center axis of the rear frame section 5 is referred to as the axis C because, like the front frame section 4, the center axis of the rear frame section 5 coincides with the center axis of the fixed section main body 20 when the rear frame section 5 is assembled to the fixed section main body 20.

The rear frame section 5 is a tubular member including an outer circumferential section 51 and an inner circumferential section 52. The outer circumferential section 51 includes a first outer circumferential section 51a, a second outer circumferential section 51b, and a third outer circumferential section 51c. The inner circumferential section 52 includes a first inner circumferential section 52a, a second inner circumferential section 52b, and an inner circumference side convex section 52c.

In the outer circumferential section 51, the first outer circumferential section 51a is smaller in diameter than the second outer circumferential section 51b and the second outer circumferential section 51b is smaller in diameter than the third outer circumferential section 51c.

In the inner circumferential section 52, the first inner circumferential section 52a is smaller in diameter than the second inner circumferential section 52b. The inner circumference side convex section 52c having the smallest diameter projecting to the radial direction inner side is provided at an end portion on the object side of the first inner circumferential section 52a.

The rear frame section 5 holds the image-side fixed lens group Gb. The image-side fixed lens group Gb includes a rear first lens Lb1 and a rear second lens Lb2. The first inner circumferential section 52a holds the rear first lens Lb1 and the rear second lens Lb2 from the object side in this order. It is preferable that, as shown in FIG. 4 and FIG. 5, the object side of the rear first lens Lb1 be in contact with the inner circumference side convex section 52c.

When the rear frame section 5 is inserted into the fixed section main body 20, the second outer circumferential section 51b is brought into contact with the fixed-side sliding surface 24 of the image-side thick section 23 of the fixed section main body 20 and, at the same time, the rear frame section 5 is inserted until an end face 23a on the image side of the fixed section main body 20 comes into contact with a step section 51d between the second outer circumferential section 51b and the third outer circumferential section 51c.

The fixed section 2 configured as explained above is formed in a tubular shape using a material having specific permeability larger than 1.0, although the material is a nonmagnetic body. Examples of such a material include austenitic stainless steel.

Figure 13:
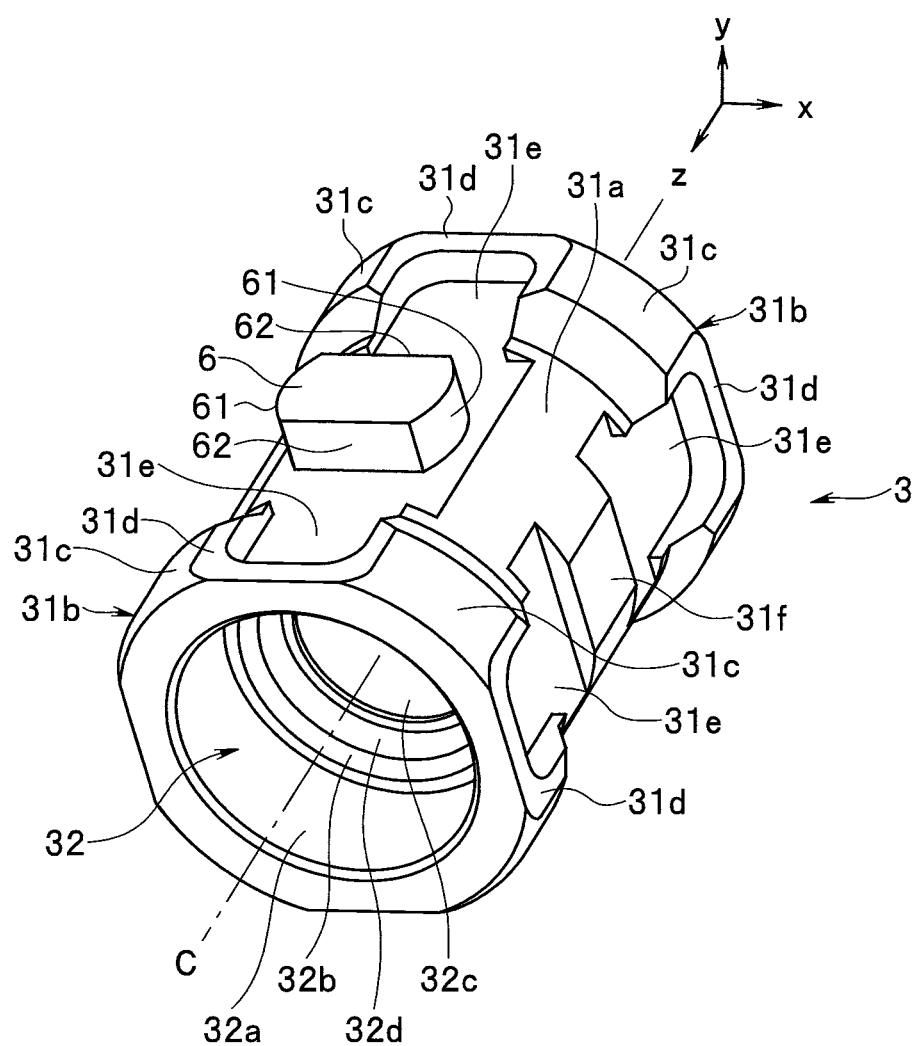
FIG. 13 is a perspective view showing a configuration of a movable section of the optical unit according to the first embodiment.
Figure 14:
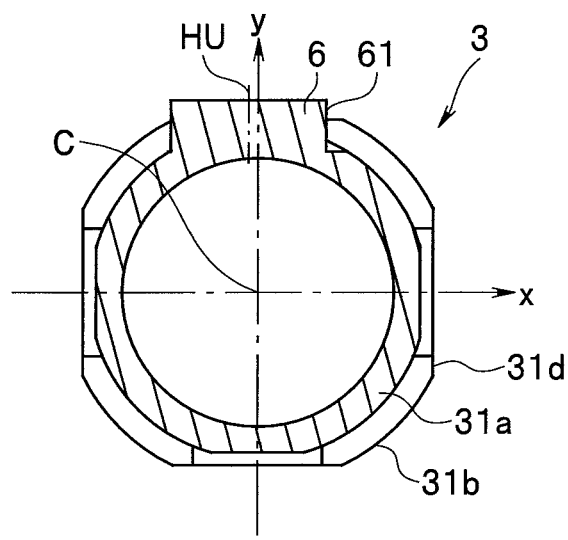
FIG. 14 is a sectional view of a movable section when viewed on a cut surface passing a VI-VI line of FIG. 15 in the first embodiment.
Figure 15:
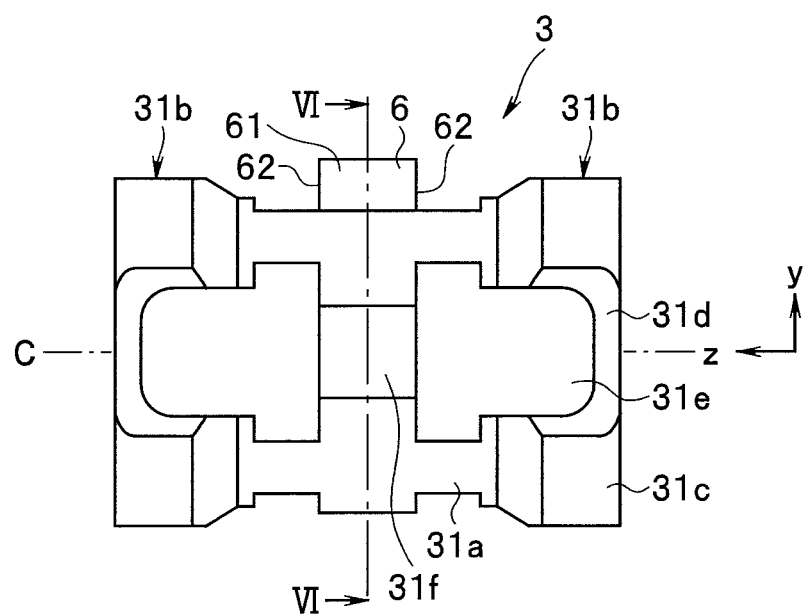
FIG. 15 is a side view showing the configuration of the movable section of the optical unit according to the first embodiment.

FIG. 13 is a perspective view showing a configuration of the movable section 3 of the optical unit 1. FIG. 14 is a sectional view of the movable section 3 when viewed on a cut surface passing a VI-VI line of FIG. 15. FIG. 15 is a side view showing the configuration of the movable section 3 of the optical unit 1.

The movable section 3 shown in FIG. 13 to FIG. 15 is configured as a tubular member including an outer circumferential section 31 and an inner circumferential section 32. In the following explanation, a center axis of the movable section 3 is also referred to as axis C. This is because, when the movable section 3 is assembled to the fixed section main body 20, the center axis of the movable section 3 coincides with the center axis of the fixed section main body 20.

The external circumferential section 31 includes a tube section 31a and two projecting edge sections 31b respectively formed at both end portions in the axis C direction of the tube section 31a and larger than the tube section 31a in diameter of an outer circumference. The tube section 31a and the projecting edge sections 31b may be configured as an integral member or may be configured as separate members.

Each of the projecting edge sections 31b includes movable-side sliding surfaces 31c, which are outer circumferential surfaces having the axis C and a center axis, and plane sections 31d formed in parts on a radial direction outer side of the projecting edge section 31b. In the case of the configuration shown in FIG. 13 to FIG. 15, the projecting edge section 31b includes four movable-side sliding surfaces 31c and four plane sections 31d alternately in a circumferential direction centering on the axis C. The four movable-side sliding surfaces 31c are disposed at equal intervals in the circumferential direction centering on the axis C. Similarly, the four plane sections 31d are also disposed at equal intervals along the circumferential direction.

The plane sections 31d of the projecting edge section 31b on one end side pass the same plane as any one of the four plane sections 31d formed in the projecting edge section 31b on the other end side in the axis C direction. In other words, the outer circumferential section 31 includes four pairs of two plane sections 31d that are formed at end portions different from one another and pass the same plane.

Step sections 31e formed further on a radial direction inner side than the tube section 31a and having plane-like outer circumferential surfaces are respectively provided among the four pairs of plane sections 31d. The rotation restricting section 6 is provided in a center in the axis C direction of the step section 31e formed between, for example, one pair of plane sections 31d, in an example shown in FIG. 13 to FIG. 15, one pair of plane sections 31d on a y-direction side among the four pairs of plane sections 31d.

At least one rotation restricting section 6 provided in the movable section 3 is disposed on an inside of at least one thinned-down section 21a among a plurality of thinned-down sections 21a and engages with the thinned-down section 21a to restrict rotation of the movable section 3 around the axis C. At this time, by setting an angle range of one rotation restricting section 6 centering on the axis C to be larger than an angle range of one magnet section 12 explained below centering on the axis C, the rotation restricting section 6 is configured to maintain a state in which the magnet section 12 is in noncontact with the fixed section 2.

As explained below, a center position HU around the axis C of the thinned-down section 21a on an upper side in a y positive direction, with which the rotation restricting section 6 in the embodiment engages, is present in a position rotated slightly further to the left in FIG. 3 than a positive direction on a y axis. Therefore, a center position around the axis C of the rotation restricting section 6 is also set to match the center position HU, that is, to be a position rotated slightly further to the left in FIG. 3 than a positive direction on the y axis.

In the rotation restricting section 6 shown in FIG. 13 to FIG. 15, at least portions in contact with the fixed section 2, that is, a surface on an x-direction side and a surface of a −x-direction side are formed as R surfaces 61 formed in an R shape around the y axis. A surface on a z-direction side and a surface on a −z-direction side of the rotation restricting section 6 are formed as planes 62 parallel to an x-y plane.

The rotation restricting section 6 may be configured as a member integral with the movable section 3 or may be configured as a member separate from the movable section 3 and fixed to the movable section 3 by bonding or the like. When the rotation restricting section 6 is configured integral with the movable section 3, there is an advantage that it is possible to reduce the number of components and reduce assembly steps. On the other hand, when the rotation restricting section 6 is separated from the movable section 3, since the movable section 3 and the rotation restricting section 6 are respectively separately manufactured, there is an advantage that shapes of the movable section 3 and the rotation restricting section 6 are simplified and machining is facilitated and component accuracy can be easily improved.

Note that, in the configuration shown in FIG. 13 to FIG. 15, the surface on the x-direction side and the surface on the −x-direction side of the rotation restricting section 6 are formed as the R surfaces 61. However, the surfaces are not limited to this and may be formed as planes parallel to a y-z plane. Similarly, in the configuration shown in FIG. 13 to FIG. 15, the surface on the z-direction side and the surface on the −z-direction side of the rotation restricting section 6 are formed as the planes 62. However, the surfaces are not limited to this and may be formed as R surfaces formed in an R shape around the y axis. In this case, the rotation restricting section 6 only has to be formed in a short columnar shape.

Further, in order to maintain the state in which the magnet section 12 and the fixed section 2 are in noncontact as explained above, length in the x direction of the rotation restricting section 6 is set to be larger than length in the x direction of the magnet section 12 disposed to hold the rotation restricting section 6.

In centers in the axis C direction of the step sections 31e formed among the other three pairs of plane sections 31d among the four pairs of plane sections 31d, cutout sections 31f, outer circumferences of which are formed in a plane shape, are each provided by cutting out a surface of the tube section 31a.

Note that, in the configuration shown in FIG. 13 to FIG. 15, one rotation restricting section 6 and three cutout sections 31f are provided. However, two or more rotation restricting sections 6 may be provided by further providing the rotation restricting sections 6 instead of the cutout sections 31f.

The magnet sections 12 configuring the voice coil motor 10 are respectively fixed to, using an adhesive or the like, one pair of step sections 31e holding the rotation restricting section 6 and three pairs of step sections 31e holding the three cutout sections 31f. The magnet section 12 disposed further on the object side than the rotation restricting section 6 and the cutout section 31f in the direction of the axis C is a first magnet 12a. The magnet section 12 disposed further on the image side than the rotation restricting section 6 and the cutout section 31f in the direction of the axis C is a second magnet 12b. Therefore, the rotation restricting section 6 is disposed between the first magnet 12a and the second magnet 12b of at least one magnet section 12.

The inner circumferential section 32 includes a first inner circumferential section 32a, a second inner circumferential section 32b, a third inner circumferential section 32c, and an inner circumference side convex section 32d. The second inner circumferential section 32b is smaller in diameter than the first inner circumferential section 32a and the third inner circumferential section 32c. The inner circumference side convex section 32d having the smallest diameter projecting to the radial direction inner side is provided between the second inner circumferential section 32b and the third inner circumferential section 32c.

The movable section 3 holds the movable lens group Gv. More specifically, the second inner circumferential section 32b of the movable section 3 holds a movable first lens Lv1 included in the movable lens group Gv. As shown in FIG. 4 and FIG. 5, it is preferable that the image side of the movable first lens Lv1 be in contact with the inner circumference side convex section 32d.

The movable section 3 performs alignment around the axis C such that the magnet sections 12 and the rotation restricting section 6 are in the same circumferential direction position as circumferential direction positions of the thinned-down sections 21a and then brings the movable-side sliding surface 31c into contact with the fixed-side sliding surface 24 and is inserted into an inside of the fixed section main body 20, for example, from the image-side thick section 23 side.

When the movable section 3 is inserted into a predetermined position on the inside of the fixed section main body 20, subsequently, as shown in FIG. 4 and FIG. 5, the rear frame section 5 is inserted into the fixed section main body 20 and the movable section 3 such that the first outer circumferential section 51a of the rear frame section 5 is opposed to the radial direction inner side of the third inner circumferential section 32c.

Consequently, at least a part of the image-side fixed lens group Gb is present on the radial direction inner side of the third inner circumferential section 32c of the movable section 3. In the first embodiment, when the movable section 3 moves to the object side most, at least a part of the object-side fixed lens group Gf is present on the radial direction inner side of the first inner circumferential section 32a of the movable section 3.

The movable section 3 configured as explained above is configured using a material such as stainless steel, aluminum, or resin.

As shown in FIG. 5, in a direction along the axis C, a distance from a position on the most object side to a position on the most image side in the movable-side sliding surface 31c of the movable section 3 is represented as L1. The distance L1 does not include a chamfered portion. Further, in the direction along the axis C, a distance from an emission surface of the object-side fixed lens group Gf held by the front frame section 4 to an incident surface of the image-side fixed lens group Gb held by the rear frame section 5 is represented as L2. At this time, in the optical unit 1, the distance L1 is longer than the distance L2 (L1>L2).

Next, a configuration of the voice coil motor 10 is explained. The voice coil motor 10 includes, as shown in FIG. 1, FIG. 4, and the like, the coil section 11 disposed in the fixed section main body 20 of the fixed section 2 and the magnet section 12 disposed in the movable section 3 to be opposed to the coil section 11. The voice coil motor 10 applies an electric current to the coil section 11 to thereby move the movable section 3 in the direction of the axis C relatively to the fixed section 2.

The coil section 11 is configured by winding a magnet wire, that is, an insulation-coated lead wire around the axis C, which is the center axis. More specifically, the coil section 11 includes, as shown in FIG. 4 and FIG. 5, the first coil 11a and the second coil 11b. The first coil 11a is configured by winding the magnet wire on the object side of an outer circumference of the tube section 21 of the fixed section main body 20. The second coil 11b is configured by winding the magnet wire on the image side of the outer circumference of the tube section 21 of the fixed section main body 20. In this way, the first coil 11a and the second coil 11b are disposed side by side in the axis C direction. Note that the coil section 11 may be formed by winding the magnet wire in advance, and the formed coil section 11 may be disposed on the outer circumference side of the tube section 21.

The first coil 11a and the second coil 11b adjacent to each other in the axis C direction are preferably electrically connected as a series circuit but may be electrically connected as a parallel circuit.

The first coil 11a and the second coil 11b respectively include, as shown in FIG. 4 and FIG. 5, plane sections 11ap and 11bp respectively opposed to the thinned-down sections 21a of the fixed section main body 20. The first coil 11a and the second coil 11b respectively include cylinder sections 11at and 11bt opposed to the tube section 21. In the first coil 11a, four plane sections 11ap and four cylinder sections 11at are alternately disposed on a cross section orthogonal to the axis C. Similarly, in the second coil 11b, four plane sections 11bp and four cylinder sections 11bt are alternately disposed on a cross section orthogonal to the axis C (see FIG. 2).

The first magnet 12a and the second magnet 12b of the magnet section 12 are fixed to the step section 31e of the movable section 3 and disposed to enter the respective thinned-down sections 21a of the fixed section 2 when the movable section 3 is inserted into the fixed section main body 20.

Four magnet sections 12 in the embodiment are provided. As shown in FIG. 1 to FIG. 5, one magnet section 12 includes the first magnet 12a and the second magnet 12b disposed side by side in the axis C direction. Therefore, the four magnet sections 12 include four first magnets 12a and four second magnets 12b.

Note that, more in general, when n is an integer equal to or larger than 2, n magnet sections 12 are disposed around the axis C with respect to the movable section 3, that is, include n first magnets 12a and n second magnets 12b. The n magnet sections 12 are each magnetically polarized in a direction crossing the axis C and disposed at every $(360/n)°$ in symmetrical positions around the axis C in the movable section 3. When the n magnet sections 12 are provided, n thinned-down sections 21a are provided in the fixed section 2. The n thinned-down sections 21a respectively house the n magnet sections 12 in a noncontact manner. Here, n represents the number of magnet sections 12 disposed in the circumferential direction centering on the axis C and may be an even number or may be an odd number but is preferably an even number as explained below.

The first coil 11a of the coil section 11 is opposed to the n first magnets 12a. The second coil 11b is opposed to the n second magnets 12b. More specifically, the first magnets 12a are disposed on an inner side of the plane section 11ap of the first coil 11a and opposed to the plane section 11ap. The second magnet 12b is disposed on an inner side of the plane section 11bp of the second coil 11b and opposed to the plane section 11bp.

The four first magnets 12a are disposed in quadrisection positions in the circumferential direction centering on the axis C, that is, positions at every 90°. Therefore, when the four first magnets 12a are viewed on a cross section orthogonal to the axis C, an interval between the first magnets 12a adjacent to each other in the circumferential direction is an equal interval. Disposition of the four second magnets 12b on the cross section orthogonal to the axis C is the same as the disposition of the first magnets 12a shown in FIG. 2. Therefore, the four second magnets 12b are also disposed in quadrisection positions in the circumferential direction centering on the axis C, that is, positions at every 90°.

Figure 16:
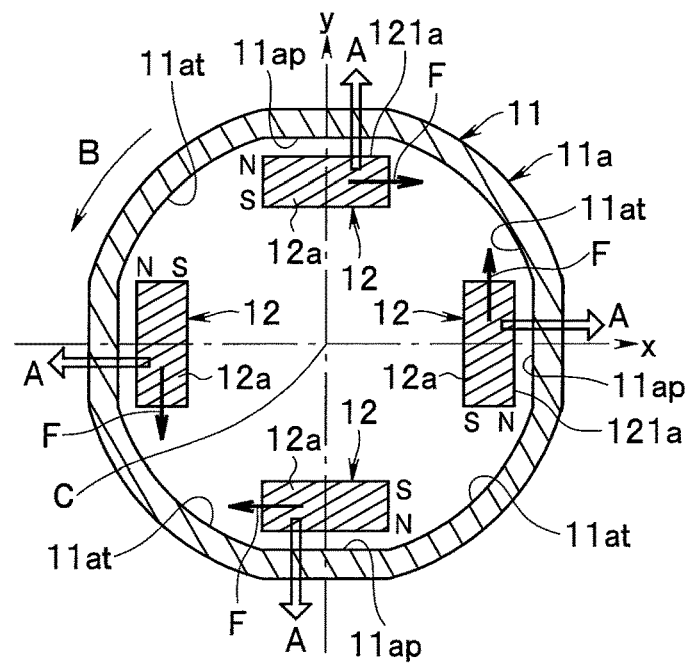
FIG. 16 is a sectional view showing a configuration of only a voice coil motor when viewed on a cut surface passing a VII-VII line shown in FIG. 4 in the first embodiment.

FIG. 16 is a sectional view showing a configuration of only the voice coil motor 10 when viewed on a cut surface passing a VII-VII line shown in FIG. 4.

In FIG. 16, forces (attraction forces F) received by the respective first magnets 12a from the fixed section 2 are indicated as black arrows. In this case, a resultant force obtained by combining the attraction forces F received by the four first magnets 12a is nearly zero. The same applies to the four second magnets 12b. Therefore, according to the first embodiment, a rotational moment centering on the axis C is nearly zero. It is possible to reduce a frictional force between the fixed section 2 and the movable section 3. As a result, driving efficiency in driving the movable section 3 is improved. Consequently, it is possible to reduce the voice coil motor 10 in size.

Figure 17:
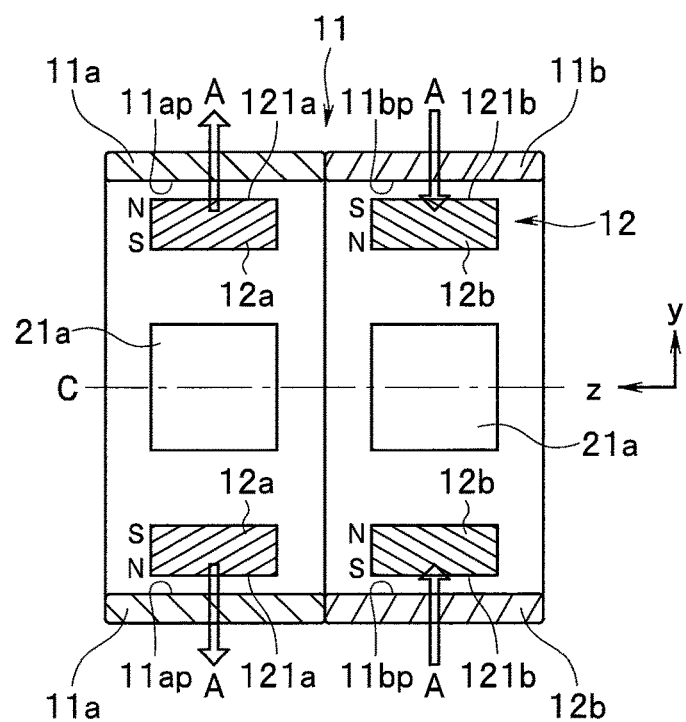
FIG. 17 is a sectional view showing only the voice coil motor on the same cut surface as the cut surface of FIG. 4 in the first embodiment.

FIG. 17 is a sectional view showing only the voice coil motor 10 on the same cut surface as the cut surface shown in FIG. 4.

As shown in FIGS. 4 and 17, length in the axis C direction of the first coil 11a is larger than length in the axis C direction of the first magnet 12a. Similarly, length in the axis C direction of the second coil 11b is larger than length in the axis C direction of the second magnet 12b. Further, length in the axis C direction from an end portion on the object side of the first coil 11a to an end portion on the image side of the second coil 11b is larger than length from an end portion on the object side of the first magnet 12a to an end portion on the image side of the second magnet 12b. By setting the lengths in this way, within a moving range of the movable section 3, it is possible to cause the first magnet 12a to be always present within the length in the axis C direction of the first coil 11a and cause the second magnet 12b to be always present within the length in the axis C direction of the second coil 11b.

As shown in FIG. 16 and FIG. 17, the first magnet 12a and the second magnet 12b forming a pair in the axis C direction are disposed to be separated. The first magnet 12a and the second magnet 12b in any pair are each magnetized in the radial direction. Magnetic polarization directions of the first magnet 12a and the second magnet 12b are opposite to each other, that is, directions of magnetic poles of the first magnet 12a and the second magnet 12b are opposite to each other.

In the case of a configuration shown in FIG. 16 and FIG. 17, in the first magnet 12a, the first coil 11a side is an N pole and an opposite side of the first coil 11a side is an S pole. In the second magnet 12b, the second coil 11b side is an S pole and an opposite side of the second coil 11b side is an N pole. In this case, the magnetic polarization directions of the first magnet 12a and the second magnet 12b are orthogonal to the axis C as indicated by white arrows A shown in FIG. 16 and FIG. 17.

Note that the magnetic polarization directions of the first magnet 12a and the second magnet 12b are not limited to the directions orthogonal to the axis C and, as explained above, more in general, only has to be directions crossing the axis C. In this case, one of the first magnet 12a and the second magnet 12b has a component in an outer radial direction centering on the axis C and the other has a component in an inner radial direction centering on the axis C.

In the first embodiment, in the first coil 11a and the second coil 11b, directions in which an electric current rotates and flows around the axis C are opposite.

Accordingly, it is preferable that a winding direction of the coil section 11 be reversed between a pair of the first magnets 12a and a pair of the second magnets 12b in the axis C direction. For example, as shown in FIG. 16, when the first coil 11a is wound in a direction of an arrow B, the second coil 11b only has to be wound in an opposite direction of the arrow B.

Alternatively, winding directions of the first coil 11a and the second coil 11b may be set the same and the first coil 11a and the second coil 11b may be connected to a driving circuit or the like such that a current direction of the first coil 11a and a current direction of the second coil 11b are opposite.

In any case, as shown in FIG. 16, when an electric current is fed to the first coil 11a in the direction of the arrow B, an electric current only has to flow to the second coil 11b in an opposite direction of the arrow B.

In the optical unit 1 configured as explained above, the movable section 3, in which the first magnets 12a are each set to be opposed to the first coil 11a, is disposed on a radial direction inner side of the fixed section main body 20 on which the first coil 11a is wound. Similarly, the movable section 3, in which the second magnets 12b are each set to be opposed to the second coil 11b, is disposed on the radial direction inner side of the fixed section main body 20 on which the second coil 11b is wound.

With such a configuration, the plane sections 11ap of the first coil 11a are each present in a magnetic field in a direction orthogonal to surfaces 121a on the outer side in a radial direction of the first magnets 12a. Similarly, the plane sections 11bp of the second coil 11b are each present in a magnetic field in a direction orthogonal to surfaces 121b on the outer side in a radial direction of the second magnets 12b.

Therefore, driving efficiency is improved and it is possible to quickly move the movable section 3. Since the surfaces 121a on the outer side in the radial direction of the first magnets 12a and the surfaces 121b on the outer side in the radial direction of the second magnets 12b are formed in a plane shape, it is possible to easily perform assembly of the optical unit 1.

When an electric current is fed to the coil section 11 of the optical unit 1, force in the axis C direction is generated in the movable section 3 by influence of a magnetic field of the magnet section 12, and the movable section 3 moves in the axis C direction with respect to the fixed section 2. For example, by controlling electric currents respectively fed to the first coil 11a and the second coil 11b, it is possible to move the movable section 3 with respect to the fixed section 2. Even in a state in which the movable section 3 is moving with respect to the fixed section 2, a surface on the outer side in a radial direction of the magnet section 12 is disposed in the thinned-down sections 21a of the fixed section main body 20.

In the optical unit 1, as shown in FIG. 5, an outer circumferential surface of the projecting edge section 31b of the movable section 3 configures the movable-side sliding surface 31c that is in contact with the fixed-side sliding surface 24 of the fixed section main body 20. By setting the fixed-side sliding surface 24 of the fixed section main body 20 and the movable-side sliding surface 31c of the movable section 3 in contact, it is possible to move the movable section 3 always in a contact state with the fixed section main body 20 and suppress inclination of the movable section 3 with respect to the fixed section 2. It is possible to accurately move the movable section 3.

Figure 18:
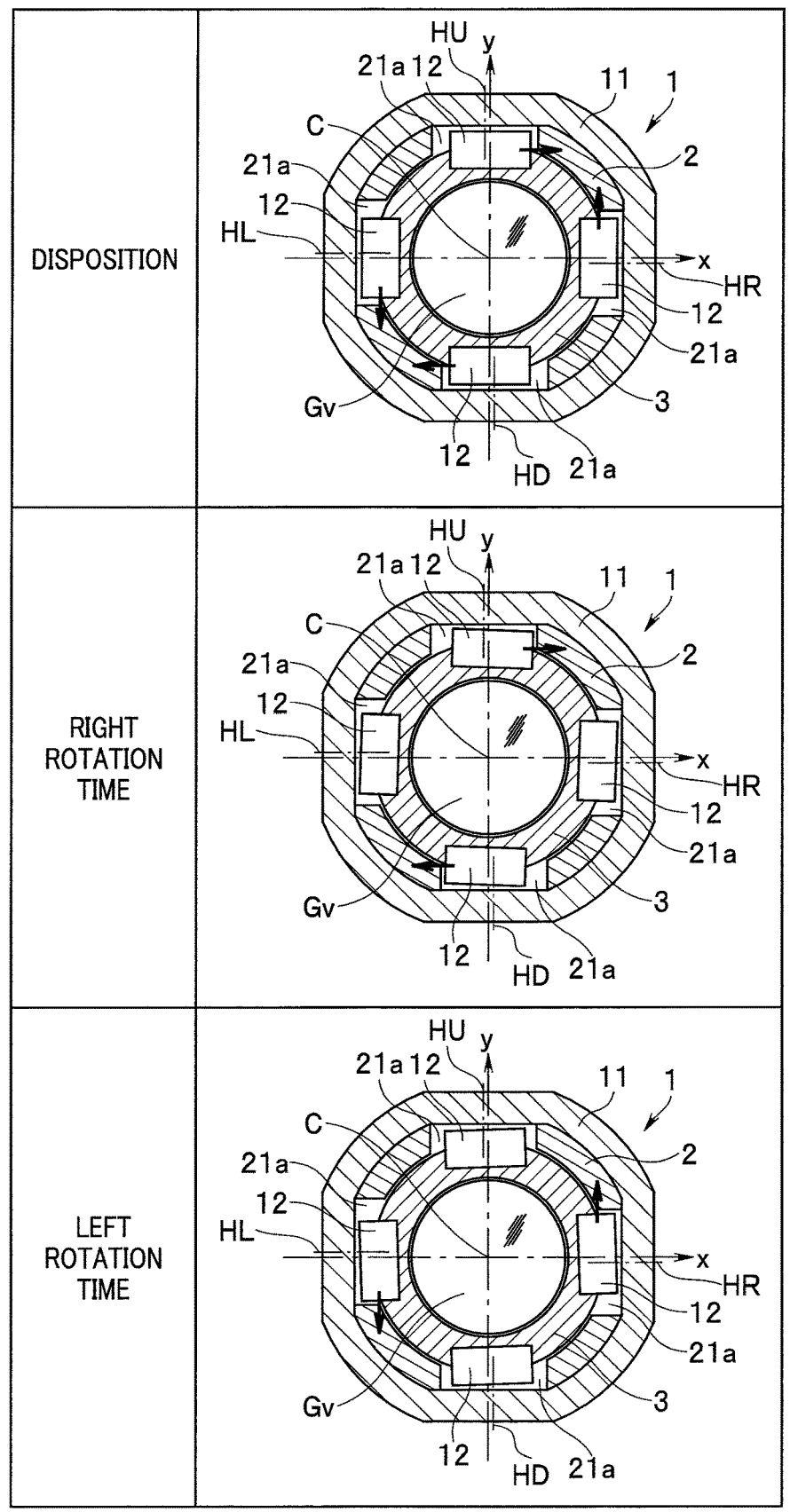
FIG. 18 is a diagram showing disposition of thinned-down sections and magnet sections of the voice coil motor around an axis C and states at right rotation time and at left rotation time.

FIG. 18 is a diagram showing disposition of the thinned-down sections 21a and the magnet sections 12 of the voice coil motor 10 around the axis C and states at right rotation time and at left rotation time.

In the embodiment, the four first magnets 12a and the four second magnets 12b are provided and n representing the number of magnet sections 12 is four, which is an even number. As explained above, the magnet sections 12 are disposed in the quadrisection positions around the axis C in the movable section 3, that is, a disposition angle between the magnet sections 12 adjacent to each other in the circumferential direction centering on the axis C is 90°.

In this way, for example, as shown in a disposition field of FIG. 18, among the four magnet sections 12 disposed around the axis C, a first magnet section 12 on the right side is disposed such that a center of the first magnet section 12 is located in a positive direction on the x axis, an origin of which is the axis C, a second magnet section 12 on the upper side is disposed such that a center of the second magnet section 12 is located in a positive direction on the y axis, an origin of which is the axis C, a third magnet section 12 on the left side is disposed such that a center of the third magnet section 12 is located in a negative direction on the x axis, and a fourth magnet section 12 on a lower side is disposed such that a center of the fourth magnet section 12 is located in a negative direction on the y axis.

The n thinned-down sections 21a are formed in asymmetrical positions around the axis C and include at least one pair of two thinned-down sections 21a adjacent to each other around the axis C, an angle around the axis C of centers of which is different from $(360/n)°$.

The asymmetrical disposition around the axis C may be achieved by performing, on each of the thinned-down sections 21a, shifting of an angle range of one thinned-down section 21a to a clockwise or counterclockwise side.

Alternatively, the asymmetrical disposition around the axis C may be achieved by performing, on each of the thinned-down sections 21a, expansion of the angle range of one thinned-down section 21a to the clockwise or counterclockwise side around the axis C. The adjacent pair of two thinned-down sections 21a may be disposed such that an angle formed by centers of the thinned-down sections 21a is larger than (360/n)° or may be disposed such that the angles formed by the centers of the thinned-down sections 21a is smaller than (360/n)°.

The four thinned-down sections 21a in the embodiment are disposed such that centers of the thinned-down sections 21a shift from the quadrisection positions around the axis C. In an example shown in FIG. 18, a center position HR around the axis C of the thinned-down section 21a on the right side in an x positive direction is present in a position further rotated slightly clockwise than the positive direction on the x axis. Therefore, in FIG. 8, the center position HR is located further on the lower side than a z-x plane. The center position HU around the axis C of the thinned-down section 21a on the upper side in a y positive direction is present in a position further rotated slightly counterclockwise than the positive direction on the y axis. A center position HL around the axis C of the thinned-down section 21a on the left side in an x negative direction is present in a position further rotated slightly clockwise than the negative direction on the x axis. A center position HD around the axis C of the thinned-down section 21a on the lower side in a y negative direction is present in a position further rotated slightly counterclockwise than the negative direction on the y axis.

In this way, the thinned-down section 21a on the right side and the thinned-down section 21a on the upper side adjacent to each other are disposed such that an angle between the center position HR and the center position HU is larger than 90°. The thinned-down section 21a on the left side and the thinned-down section 21a on the lower side adjacent to each other are disposed such that an angle between the center position HL and the center position HD is larger than 90°.

Note that, from another perspective, the thinned-down section 21a on the upper side and the thinned-down section 21a on the left side adjacent to each other are disposed such that the angle between the center position HU and the center position HL is smaller than 90° and the thinned-down section 21a on the lower side and the thinned-down section 21a on the right side adjacent to each other are disposed such that the angle between the center position HD and the center position HR is smaller than 90°.

In the case of the disposition in the embodiment, the magnet sections 12, the fixed section 2, and the coil section 11 are symmetrical with respect to the axis C and, in the sectional view shown in FIG. 18, symmetrical with respect to an intersection of the x axis and the y axis.

A distance from the magnet section 12 on the right side to the tube section 21 of the fixed section 2 formed using a material, specific permeability of which is larger than 1.0, is smaller on the upper side and larger on the lower side. Therefore, a counterclockwise rotational moment acts on the magnet section 12 on the right side as indicated by a black arrow in the disposition field of FIG. 18. Similarly, a clockwise rotational moment acts on the magnet section 12 on the upper side, a counterclockwise rotational moment acts on the magnet section 12 on the left side, and a clockwise rotational moment acts on the magnet section 12 on the lower side as indicated by black arrows in the disposition field of FIG. 18.

At this time, in neutral positions shown in the disposition field of FIG. 18, the rotational moments acting on the four magnet sections 12 can cancel one another and suppress occurrence of the rotational moments. Therefore, it is possible to reduce frictional resistance at the time when the movable section 3 slides in the fixed section 2 and improve driving efficiency.

As explained above, the rotation restricting section 6 engages with the thinned-down sections 21a and restricts the rotation around the axis C of the movable section 3. However, if the rotation restricting section 6 engages with the thinned-down sections 21a without a gap, it is difficult for the movable section 3 to smoothly slide in the axis C direction. Therefore, an angle range around the axis C of one rotation restricting section 6 is set slightly smaller than an angle range around the axis C of one thinned-down section 21a to enable the movable section 3 to smoothly move in the axis C direction while maintaining a state in which the magnet section 12 is in noncontact with the fixed section 2.

In the case of such a configuration, the movable section 3 can slightly rotate around the axis C.

A right rotation time field of FIG. 18 shows a state in which the movable section 3 rotates to the right centering on the axis C.

At this time, the magnet sections 12 on the upper side and the lower side lean in the thinned-down sections 21a and clockwise rotational moments act as indicated by black arrows in the right rotation time field of FIG. 18. Therefore, a clockwise rotational moment acts on the movable section 3. However, the magnet sections 12 on the right side and the left side approach centers of the thinned-down sections 21a, and rotational moments decrease or do not act. In this way, the rotational moments effectively act on, for example, two among the four magnet sections 12.

Accordingly, compared with when equal disposition in which the centers of the thinned-down sections 21a are quadrisection positions around the axis C is performed, it is possible to suppress the rotational moments to, for example, approximately a half Consequently, it is possible to improve driving efficiency at the time when the movable section 3 rotates to the right.

A left rotation time field of FIG. 18 shows a state in which the movable section 3 rotates to the left centering on the axis C.

At this time, the magnet sections 12 on the right side and the left side lean in the thinned-down sections 21a and counterclockwise rotational moments act as indicated by black arrows in the left rotation time field of FIG. 18. Therefore, a counterclockwise rotational moment acts on the movable section 3. However, the magnet sections 12 on the upper side and the lower side approach centers of the thinned-down sections 21a, and rotational moments decrease or do not act. In this way, the rotational moments effectively act on, for example, two among the four magnet sections 12. Accordingly, compared with when equal disposition in which the centers of the thinned-down sections 21a are quadrisection positions around the axis C is performed, it is possible to suppress the rotational moments to, for example, approximately a half. Consequently, it is possible to improve driving efficiency at the time when the movable section 3 rotates to the left.

According to such a first embodiment, the plurality of magnet sections 12 are disposed in the symmetrical positions around the axis C, the plurality of thinned-down sections 21a for housing the plurality of magnet sections 12 are formed in the asymmetrical positions around the axis C, and the angle around the axis C of at least an adjacent pair of thinned-down sections 21a is different from (360/n)°. Accordingly, it is possible to reduce a rotational moment and improve driving efficiency of the movable section 3 and reduce the voice coil motor 10 in size. Therefore, it is possible to realize a reduction in the size and a reduction in the weight of an actuator that moves the movable lens group Gv to advance and retract.

A state in which the plurality of magnet sections 12 are in noncontact with the fixed section 2 is maintained by the rotation restricting section 6. Accordingly, a frictional force does not occur between the magnet sections 12 and the fixed section 2 and it is possible to further improve the driving efficiency. It is possible to prevent breakage of the magnet sections 12.

At this time, since one rotation restricting section 6 is provided in the embodiment, it is possible to realize a reduction in size and a reduction in weight compared with when a plurality of rotation restricting sections 6 are provided. Further, by providing one rotation restricting section 6, accuracy requested for components is not set higher than necessary. It is possible to reduce manufacturing cost for an optical unit.

Further, the fixed section 2 is formed using the material, the specific permeability of which is larger than 1.0. Accordingly, an attraction force F is generated between the fixed section 2 and the magnet sections 12. It is possible to stabilize the movable section 3 in the position at the right rotation time or the position at the left rotation time in FIG. 18. Consequently, it is possible to suppress rotation around the axis C when the movable section 3 advances and retracts in the axis C direction.

The coil section 11 is configured by winding the magnet wire around the axis C. Accordingly, a sliding axis of the movable section 3 and an action axis of a propulsive force generated by the voice coil motor 10 can be set the same. It is possible to reduce swinging at the time when the movable section 3 advances and retracts and stabilize driving of the actuator.

The first magnet 12a and the second magnet 12b, the magnetic polarization directions of which are opposite to each other, are provided and the directions of the electric currents flowing to the first coil 11a and the second coil 11b are set opposite. Accordingly, a driving force of the voice coil motor 10 increases and it is possible to improve stability of operation.

Further, the rotation restricting section 6 is disposed between the first magnet 12a and the second magnet 12b. Accordingly, the rotation restricting section 6 is disposed substantially in a center of gravity position in the axis C direction of the movable section 3. It is possible to more stably restrict the rotation of the movable section 3.

The angle range of one rotation restricting section 6 centering on the axis C is set larger than the angle range of one magnet section 12. Therefore, it is possible to surely maintain a state in which the magnet sections 12 and the fixed section 2 are in noncontact.

In addition, the portion of the rotation restricting section 6 in contact with the fixed section 2 is formed as the R surface 61 formed in the R shape. Accordingly, it is possible to reduce a contact area of the fixed section 2 and the rotation restricting section 6 and reduce a frictional force. It is possible to improve driving efficiency of the actuator.

Since the number n of the magnet sections 12 is set to an even number, the number of thinned-down sections 21a for housing the magnet sections 12 are also an even number. Accordingly, all of the plurality of thinned-down sections 21a can configure one pair of adjacent two thinned-down sections 21a. Therefore, even if the individual thinned-down sections 21a are asymmetrically disposed around the axis C, it is possible to symmetrically dispose the thinned-down sections 21a in unit of a pair around the axis C. By symmetrically disposing the thinned-down sections 21a in unit of a pair, symmetry of distribution of magnetism passing through the fixed section 2, the specific permeability of which is larger than 1.0, is improved. It is possible to more stably drive the actuator.

Further, the fixed-side sliding surface 24 of the fixed section main body 20 and the movable-side sliding surface 31c of the movable section 3 are in contact even during operation of the movable section 3. Accordingly, it is possible to suppress inclination of the movable section 3 with respect to the fixed section 2. It is possible to accurately move the movable section 3.

When the fixed section 2 is configured as a combination of three components, that is, the fixed section main body 20, the front frame section 4, and the rear frame section 5, it is possible to set the number of components relatively small and reduce assembly steps. It is possible to realize a reduction in cost. Further, since the fixed section 2 is divided into the three components, there is an advantage that flexibility of design of the respective components increases and flexibility of design of the fixed section 2 increases.

In addition, the fixed-side sliding surface 24 of the fixed section 2 is formed to be divided in the circumferential direction. Accordingly, it is possible to achieve a reduction in the size and a reduction in the weight of the optical unit 1.

Second Embodiment

Figure 19:
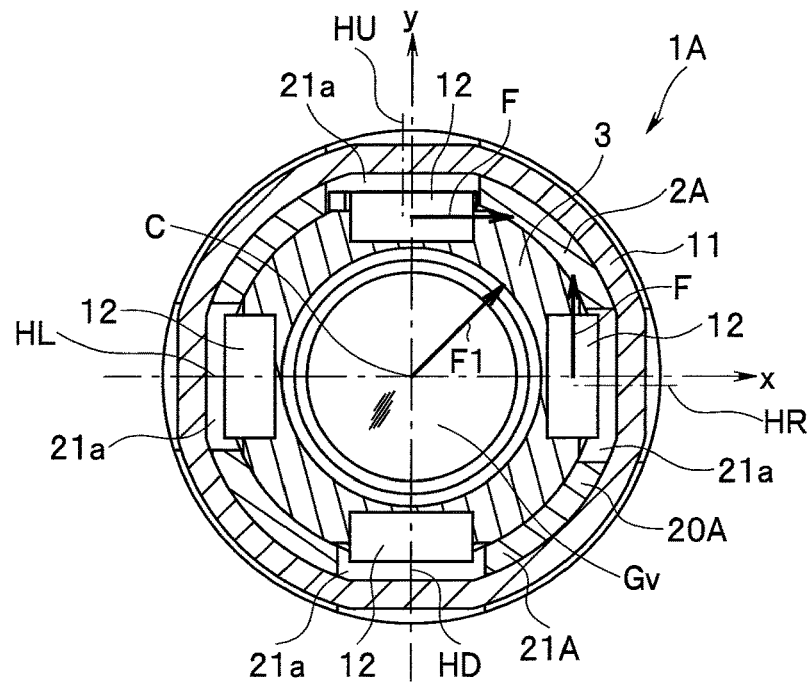
FIG. 19 is a sectional view of a configuration of an optical unit according to a second embodiment of the present invention when viewed on a cut surface perpendicular to the axis C.
Figure 20:
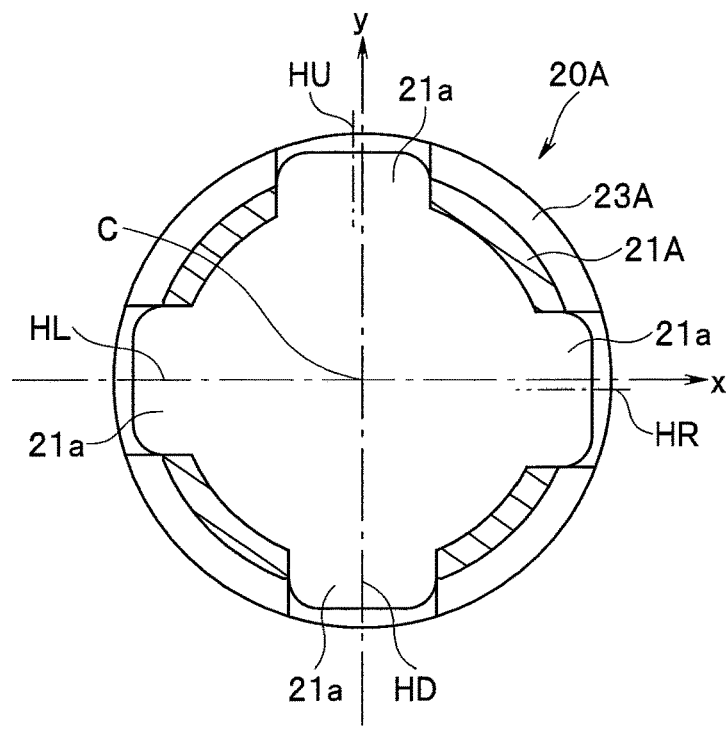
FIG. 20 is a sectional view of a fixed section main body when viewed on a cut surface passing a VIII-VIII line shown in FIG. 21 in the second embodiment.
Figure 21:
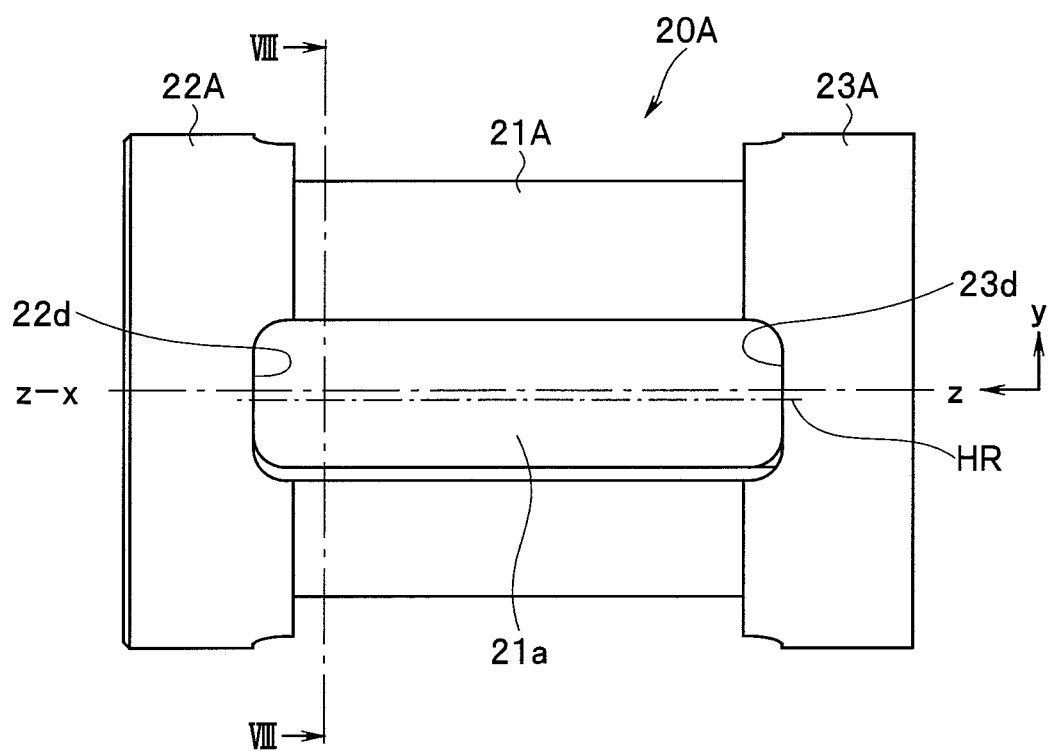
FIG. 21 is a side view showing a configuration of the fixed section main body of the optical unit according to the second embodiment.
Figure 22:
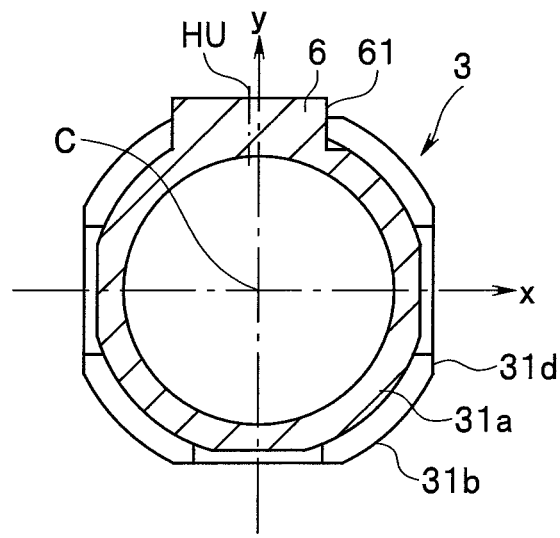
FIG. 22 is a sectional view of a movable section when viewed on a cut surface passing a IX-IX line shown in FIG. 23 in the second embodiment.
Figure 23:
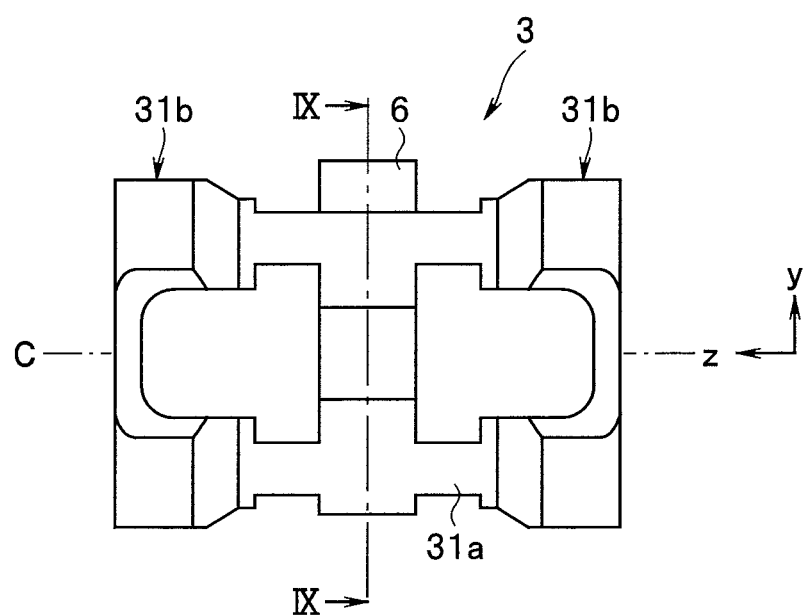
FIG. 23 is a side view showing a configuration of a movable section of the optical unit according to the second embodiment.

FIG. 19 to FIG. 23 show a second embodiment of the present invention. FIG. 19 is a sectional view of a configuration of an optical unit 1A when viewed on a cut surface perpendicular to the axis C. FIG. 20 is a sectional view of a fixed section main body 20A when viewed on a cut surface passing a VIII-VIII line shown in FIG. 21. FIG. 21 is a side view showing a configuration of the fixed section main body 20A of the optical unit 1A. FIG. 22 is a sectional view of the movable section 3 when viewed on a cut surface passing a IX-IX line shown in FIG. 23. FIG. 23 is a side view showing a configuration of the movable section 3 of the optical unit 1A according to the second embodiment.

In the second embodiment, explanation of the same portions as the portions in the first embodiment explained above is omitted as appropriate by, for example, denoting the portions with the same reference numerals and signs. Only differences are mainly explained.

In the embodiment, disposition of the thinned-down sections 21a in the fixed section main body 20A of the fixed section 2A is differentiated from the disposition in the first embodiment explained above.

In other words, as shown in FIG. 2, FIG. 18, and the like, all of the centers of the four thinned-down sections 21a in the first embodiment are present in the quadrisection positions around the axis C, that is, positions deviating from the x axis and the y axis. In contrast, in the embodiment, as shown in FIG. 19 to FIG. 21, only two thinned-down sections 21a among the four thinned-down sections 21a are in positions deviating from the quadrisection positions around the axis C.

More specifically, the center position HR around the axis C of the thinned-down section 21a on the right side in the x positive direction of a tube section 21A in the fixed section main body 20A is present in a position further rotated slightly clockwise than the positive direction on the x axis. Therefore, in FIG. 21, the center position HR is located further on the lower side than the z-x plane. The center position HU around the axis C of the thinned-down section 21a on the upper side in the y positive direction is present in a position further rotated slightly counterclockwise than the positive direction on the y axis.

In contrast, the center position HL around the axis C of the thinned-down section 21a on the left side in the x negative direction is present on the x axis. The center position HD around the axis C of the thinned-down section 21a on the lower side in the y negative direction is present on the y axis.

As shown in FIG. 21, both of the U-shaped cutout section 22d of an object-side thick section 22A and the U-shaped cutout section 23d of an image-side thick section 23A are disposed in circumferential direction positions corresponding to the thinned-down sections 21a.

In this way, in the embodiment, only one pair of the thinned-down section 21a on the right side and the thinned-down section 21a on the upper side is disposed in positions deviating from the quadrisection positions around the axis C.

As shown in FIG. 22 and FIG. 23, a configuration of the movable section 3 is the same as the configuration in the first embodiment explained above. Further, as shown in FIG. 19, a configuration of the voice coil motor 10 is also the same as the configuration in the first embodiment explained above.

In the case of the embodiment, a direction of a resultant force F1 of the attraction forces F received by the magnet section 12, that is, the first magnet 12a and the second magnet 12b from the fixed section 2A is a radial direction of the movable section 3 as shown in FIG. 19. A rotational moment centering on the axis C is nearly zero.

According to such a second embodiment, at least one pair of the thinned-down sections 21a is disposed in positions deviating from the quadrisection positions around the axis C. Accordingly, it is possible to achieve substantially the same effects as the effects in the first embodiment explained above.

Further, according to the second embodiment, it is possible to gather, in one direction (the direction of the resultant force F1 of the attraction forces F), backlash due to sliding of the fixed section 2A and the movable section 3 and suppress a tilt of the movable section 3 around an axis orthogonal to the axis C and a shift of the movable section 3 in a direction parallel to the axis C.

Third Embodiment

Figure 24:
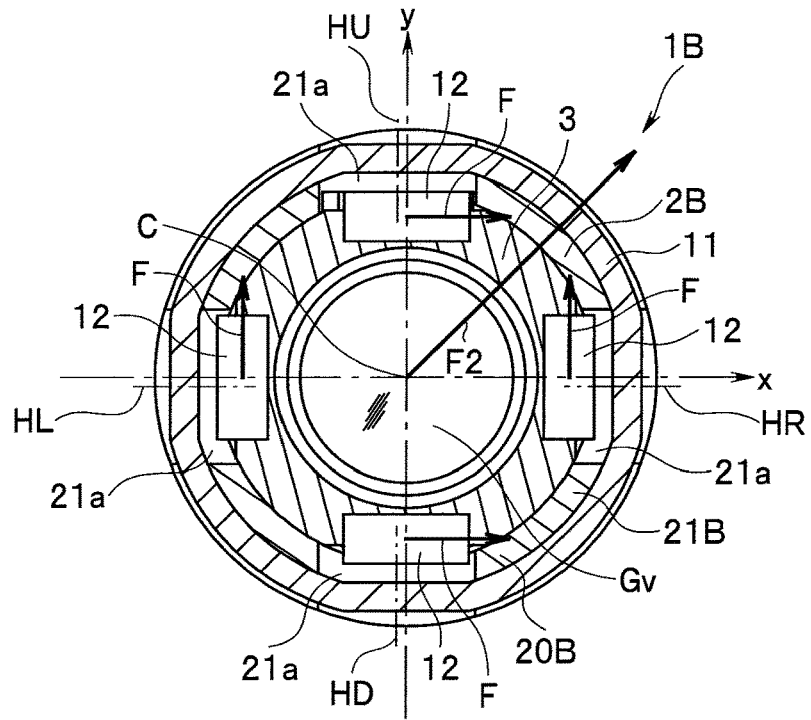
FIG. 24 is a sectional view of a configuration of an optical unit according to a third embodiment of the present invention when viewed on a cut surface perpendicular to the axis C.
Figure 25:
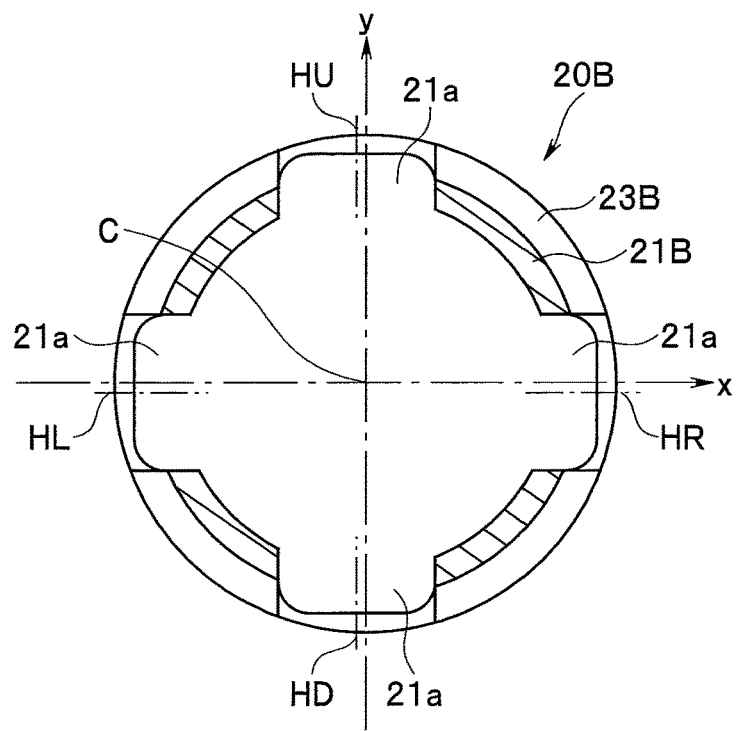
FIG. 25 is a sectional view of a fixed section main body when viewed on a cut surface passing a X-X line shown in FIG. 26 in the third embodiment.
Figure 26:
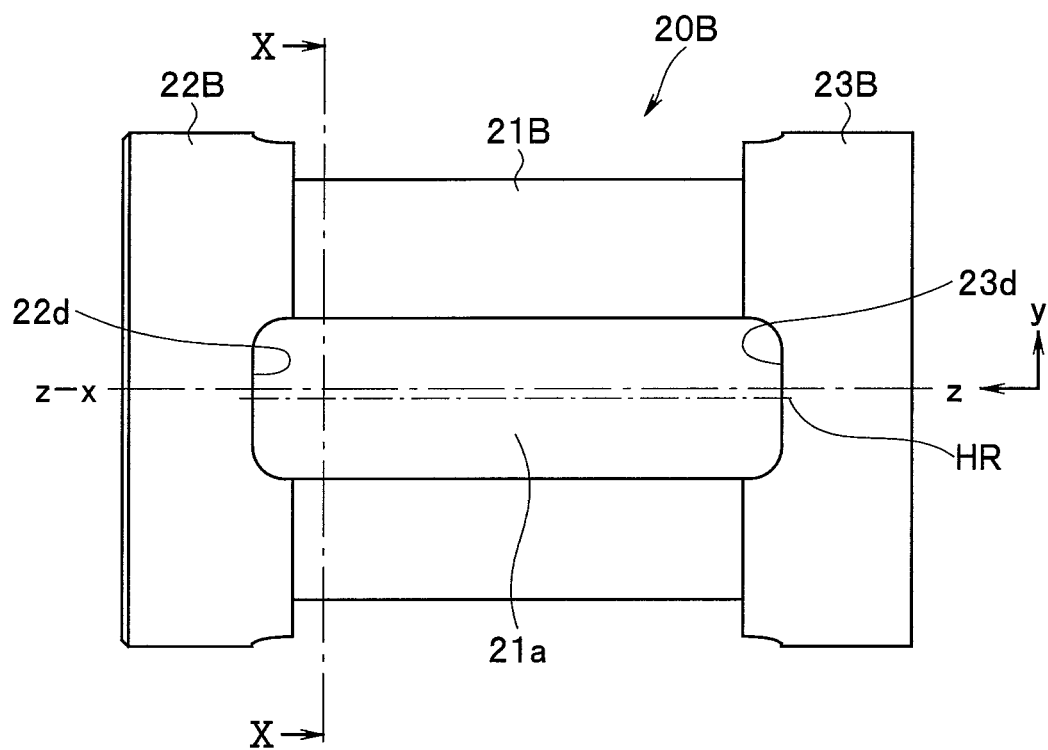
FIG. 26 is a side view showing a configuration of a fixed section main body of the optical unit according to the third embodiment.
Figure 27:
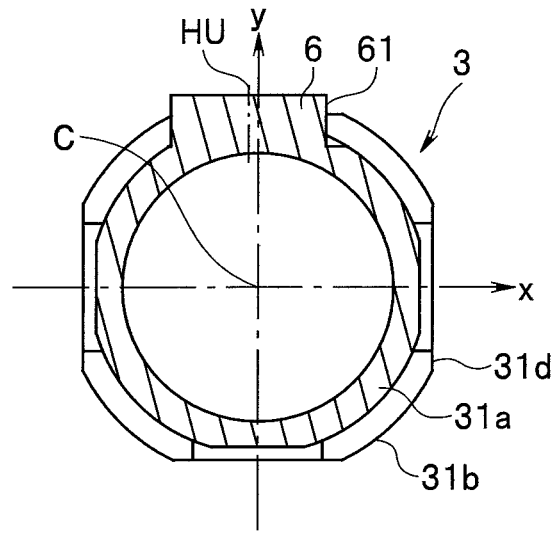
FIG. 27 is a sectional view of a movable section when viewed on a cut surface passing a XI-XI line shown in FIG. 28 in the third embodiment.
Figure 28:
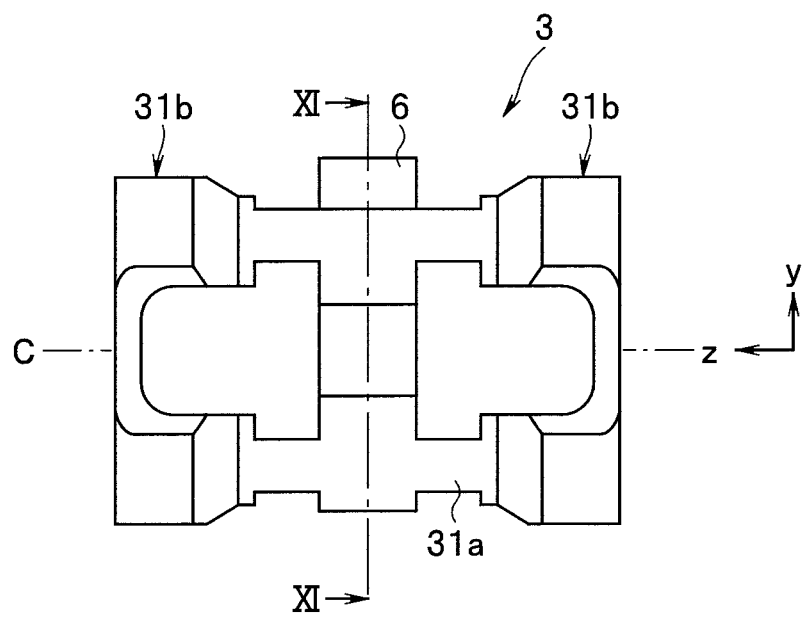
FIG. 28 is a side view showing a configuration of the movable section of the optical unit according to the third embodiment.

FIG. 24 to FIG. 28 show a third embodiment of the present invention. FIG. 24 is a sectional view of a configuration of an optical unit 1B when viewed on a cut surface perpendicular to the axis C. FIG. 25 is a sectional view of a fixed section main body 20B when viewed on a cut surface passing a X-X line shown in FIG. 26. FIG. 26 is a side view showing a configuration of a fixed section main body 20B of the optical unit 1B. FIG. 27 is a sectional view of the movable section 3 when viewed on a cut surface passing a XI-XI line shown in FIG. 28. FIG. 28 is a side view showing a configuration of the movable section 3 of the optical unit 1B.

In the third embodiment, explanation of the same portions as the portions in the first and second embodiments explained above is omitted as appropriate by, for example, denoting the portions with the same reference numerals and signs. Only differences are mainly explained.

In the embodiment, disposition of the thinned-down sections 21a in the fixed section main body 20B of a fixed section 2B is differentiated from the disposition in the first embodiment explained above.

In other words, as shown in FIGS. 24 to 26, among the four thinned-down sections 21a provided in a tube section 21B of the fixed section main body 20B, disposition of the thinned-down section 21a on the right side and the thinned-down section 21a on the upper side is the same as the disposition in the first embodiment explained above. However, disposition of the thinned-down section 21a on the left side and the thinned-down section 21a on the lower side is different from the disposition in the first embodiment explained above.

More specifically, the center position HR around the axis C of the thinned-down section 21a on the right side in the x positive direction is present in a position further rotated slightly clockwise than the positive direction on the x axis. Therefore, in FIG. 26, the center position HR is located further on the lower side than the z-x plane. The center position HU around the axis C of the thinned-down section 21a on the upper side in the y positive direction is present in a position further rotated slightly counterclockwise than the positive direction on the y axis.

The center position HL around the axis C of the thinned-down section 21a on the left side in the x negative direction is present in a position further rotated slightly counterclockwise than the negative direction on the x axis. The center position HD around the axis C of the thinned-down section 21a on the lower side in the y negative direction is present in a position further rotated slightly clockwise than the negative direction on the y axis.

As shown in FIG. 26, both of the U-shaped cutout section 22d of an object-side thick section 22B and the U-shaped cutout section 23d of an image-side thick section 23B are disposed in circumferential direction positions corresponding to the thinned-down section 21a.

In this way, in the embodiment, all of the four thinned-down sections 21a are disposed in positions deviating from the quadrisection positions around the axis C. However, a direction of the deviation from the quadrisection positions is different from the direction in the first embodiment.

As shown in FIG. 27 and FIG. 28, a configuration of the movable section 3 is the same as the configuration in the first embodiment explained above. Further, as shown in FIG. 24, a configuration of the voice coil motor 10 is also the same as the configuration in the first embodiment explained above.

In the case of the embodiment, a direction of a resultant force F2 of the attraction forces F received by the magnet section 12, that is, the first magnet 12a and the second magnet 12b from the fixed section 2B is the radial direction of the movable section 3 as shown in FIG. 24. A rotational moment centering on the axis C is nearly zero.

According to such a third embodiment, although the configuration is different, it is possible to achieve substantially the same effects as the effects in the first embodiment explained above.

Further, according to the third embodiment, it is possible to gather, in one direction (the direction of the resultant force F2 of the attraction forces F), backlash due to sliding of the fixed section 2B and the movable section 3 and suppress a tilt of the movable section 3 around an axis orthogonal to the axis C and a shift of the movable section 3 in a direction parallel to the axis C.

Fourth Embodiment

Figure 29:
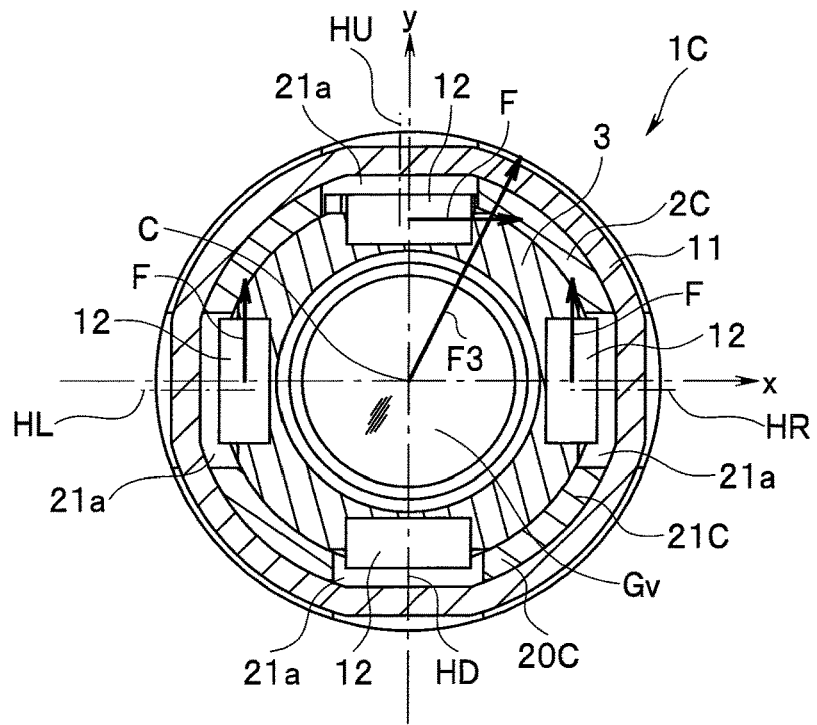
FIG. 29 is a sectional view of a configuration of an optical unit according to a fourth embodiment of the present invention when viewed on a cut surface perpendicular to the axis C.
Figure 30:
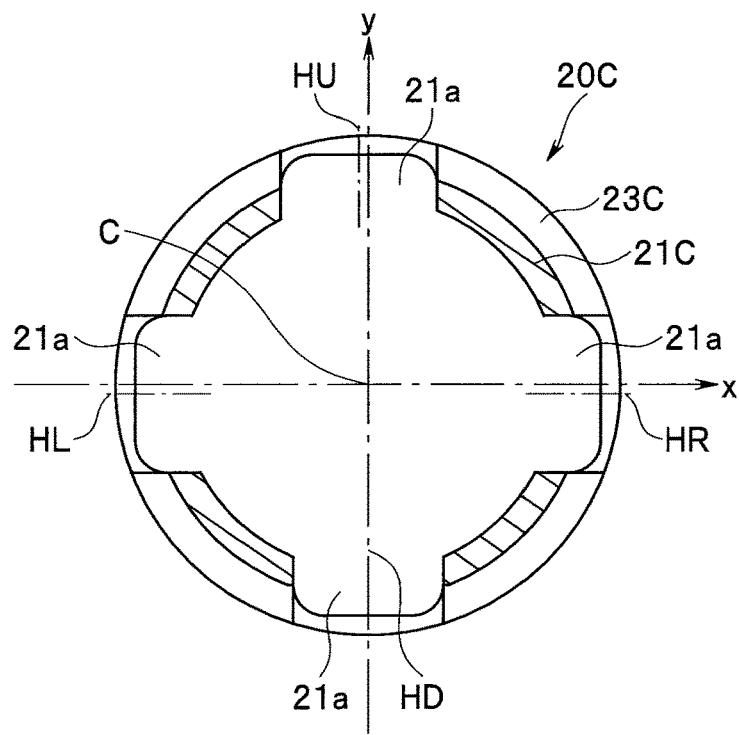
FIG. 30 is a sectional view of a fixed section main body when viewed on a cut surface passing a XII-XII line shown in FIG. 31 in the fourth embodiment.
Figure 31:
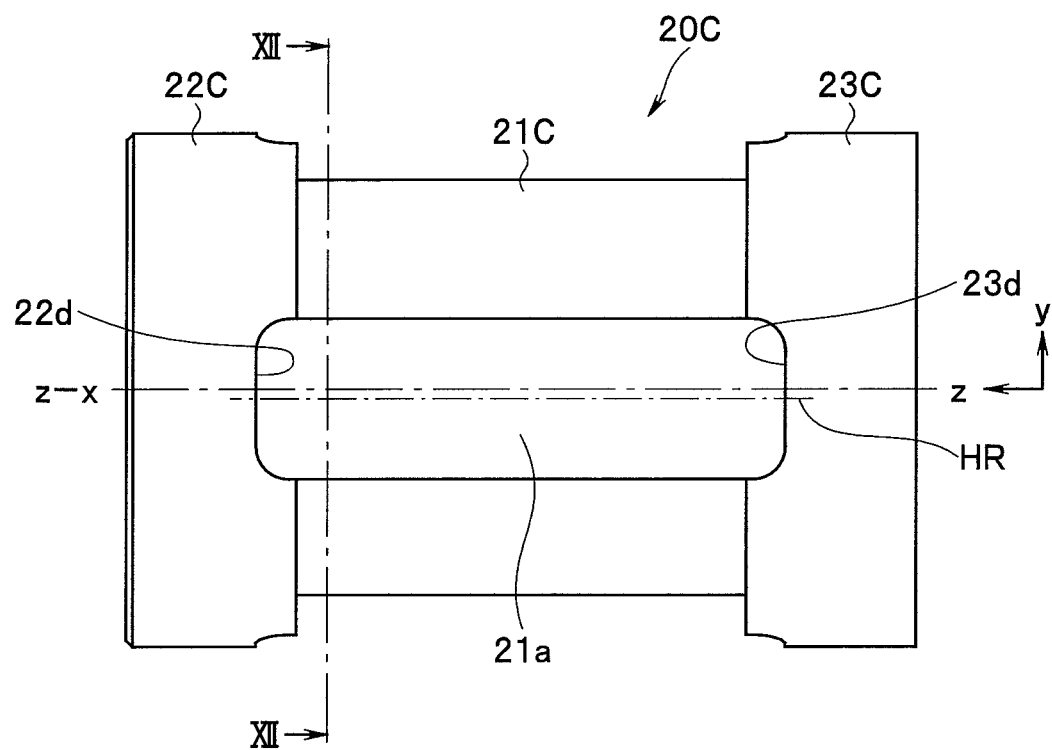
FIG. 31 is a side view showing a configuration of the fixed section main body of the optical unit according to the fourth embodiment.
Figure 32:
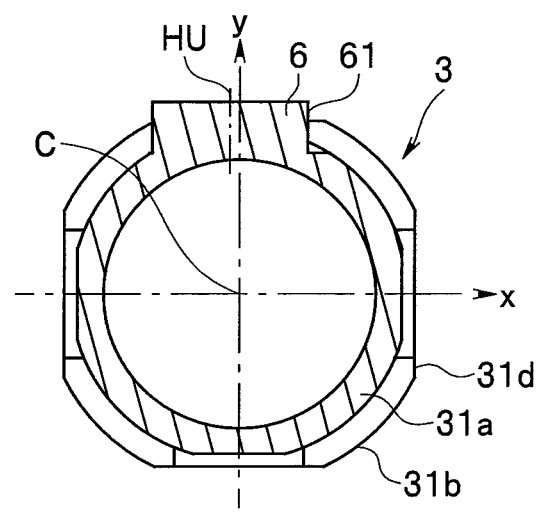
FIG. 32 is a sectional view of a movable section when viewed on a cut surface passing a XIII-XIII line shown in FIG. 33 in the fourth embodiment.
Figure 33:
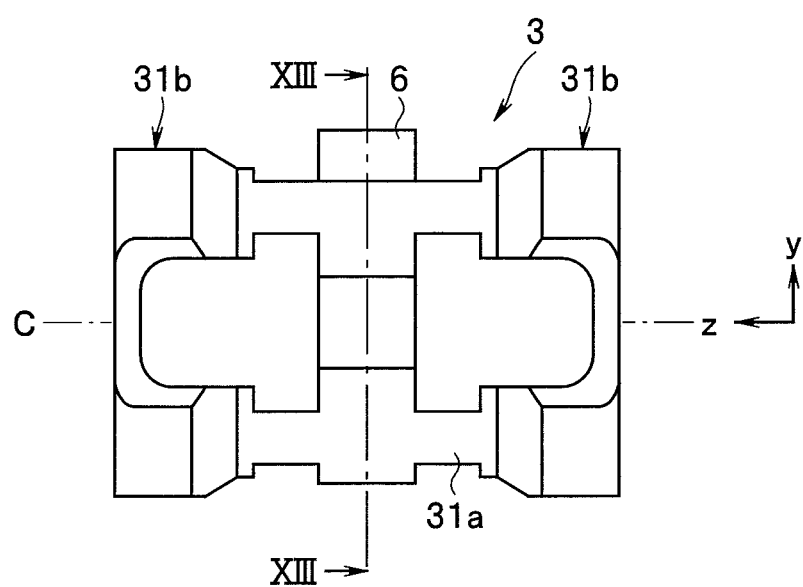
FIG. 33 is a side view showing a configuration of the movable section of the optical unit according to the fourth embodiment.

FIG. 29 to FIG. 33 show a fourth embodiment of the present invention. FIG. 29 is a sectional view of a configuration of an optical unit 1C when viewed on a cut surface perpendicular to the axis C. FIG. 30 is a sectional view of a fixed section main body 20C when viewed on a cut surface passing a XII-XII line shown in FIG. 31. FIG. 31 is a side view showing a configuration of the fixed section main body 20C of the optical unit 1C. FIG. 32 is a sectional view of the movable section 3 when viewed on a cut surface passing a XIII-XIII line shown in FIG. 33. FIG. 33 is a side view showing a configuration of the movable section 3 of the optical unit 1C.

In the fourth embodiment, explanation of the same portions as the portions in the first to third embodiments explained above is omitted as appropriate by, for example, denoting the portions with the same reference numerals and signs. Only differences are mainly explained.

In the embodiment, disposition of the thinned-down sections 21a in the fixed section main body 20C of a fixed section 2C is differentiated from the disposition in the third embodiment explained above.

In other words, as shown in FIGS. 29 to 31, among the four thinned-down sections 21a provided in a tube section 21C of the fixed section main body 20C, disposition of the thinned-down section 21a on the right side, the thinned-down section 21a on the upper side, and the thinned-down section 21a on the left side is the same as the disposition in the third embodiment explained above. However, disposition of the thinned-down section 21a on the lower side is different from the disposition in the third embodiment explained above.

More specifically, the center position HR around the axis C of the thinned-down section 21a on the right side in the x positive direction is present in a position further rotated slightly clockwise than the positive direction on the x axis. Therefore, in FIG. 31, the center position HR is located further on the lower side than the z-x plane. The center position HU around the axis C of the thinned-down section 21a on the upper side in the y positive direction is present in a position further rotated slightly counterclockwise than the positive direction on the y axis. Further, the center position HL around the axis C of the thinned-down section 21a on the left side in the x negative direction is present in a position further rotated slightly counterclockwise than the negative direction on the x axis.

In contrast, the center position HD around the axis C of the thinned-down section 21a on the lower side in the y negative direction is present on the y axis.

As shown in FIG. 31, both of the U-shaped cutout section 22d of an object-side thick section 22C and the U-shaped cutout section 23d of an image-side thick section 23C are disposed in circumferential direction positions corresponding to the thinned-down section 21a.

In this way, the embodiment is different from the third embodiment in that three of the four thinned-down sections 21a are disposed in positions deviating from the quadrisection positions around the axis C but the remaining one thinned-down section 21a is disposed in the quadrisection position around the axis C.

As shown in FIG. 32 and FIG. 33, a configuration of the movable section 3 is the same as the configuration in the first embodiment explained above. Further, as shown in FIG. 29, a configuration of the voice coil motor 10 is also the same as the configuration in the first embodiment.

In the case of the embodiment, a direction of a resultant force F3 of the attraction forces F received by the magnet section 12, that is, the first magnet 12a and the second magnet 12b from the fixed section 2C is the radial direction of the movable section 3 as shown in FIG. 29. Although a rotational moment centering on the axis C is generated, since a part of the rotational moment is in an opposite direction and offset, it is possible to suppress rotation of the movable section 3 around the axis C.

According to such a fourth embodiment, since at least one pair of the thinned-down sections 21a is disposed in positions deviating from the quadrisection positions around the axis C, it is possible to achieve substantially the same effects as the effects in the first embodiment explained above.

Further, according to the fourth embodiment, it is possible to gather, in one direction (the direction of the resultant force F3 of the attraction forces F), backlash due to sliding of the fixed section 2C and the movable section 3 and suppress a tilt of the movable section 3 around an axis orthogonal to the axis C and a shift of the movable section 3 in a direction parallel to the axis C.

Fifth Embodiment

Figure 34:
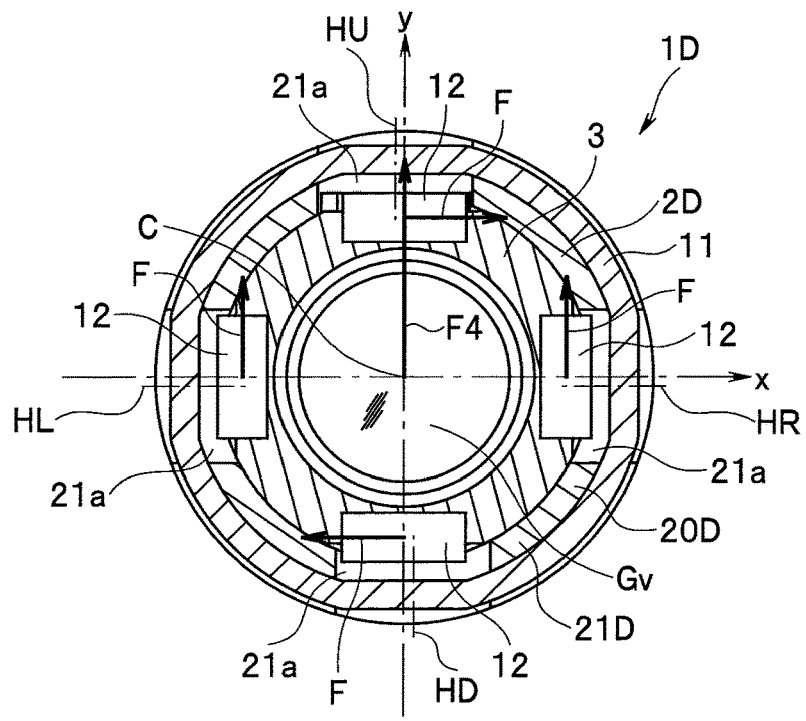
FIG. 34 is a sectional view of a configuration of an optical unit according to a fifth embodiment of the present invention when viewed on a cut surface perpendicular to the axis C.
Figure 35:
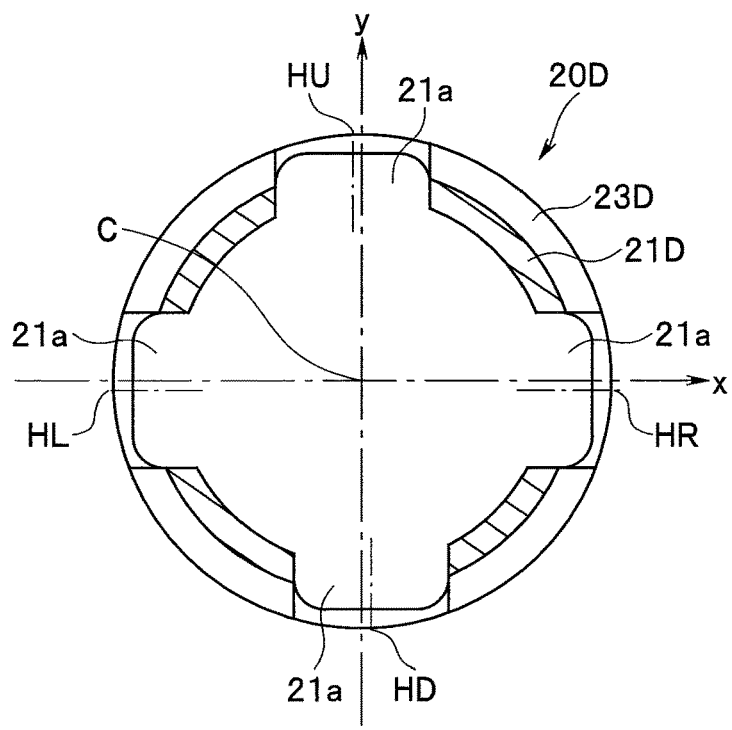
FIG. 35 is a sectional view of a fixed section main body when viewed on a cut surface passing a XIV-XIV line shown in FIG. 36 in the fifth embodiment.
Figure 36:
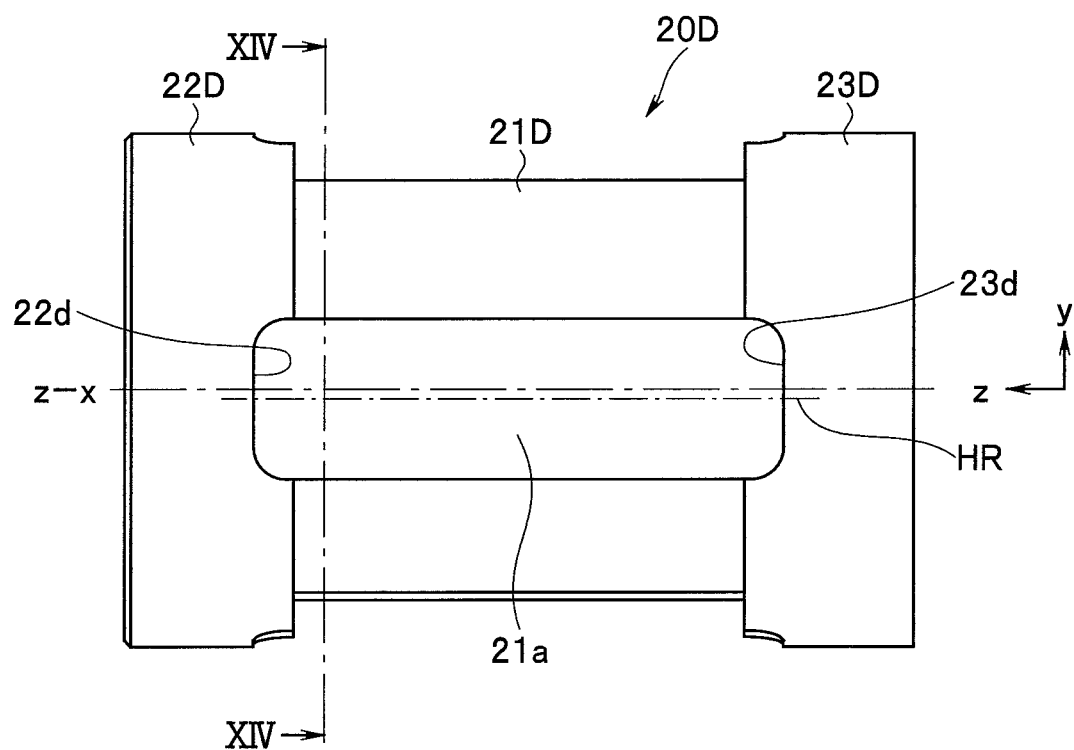
FIG. 36 is a side view showing a configuration of the fixed section main body of the optical unit according to the fifth embodiment.
Figure 37:
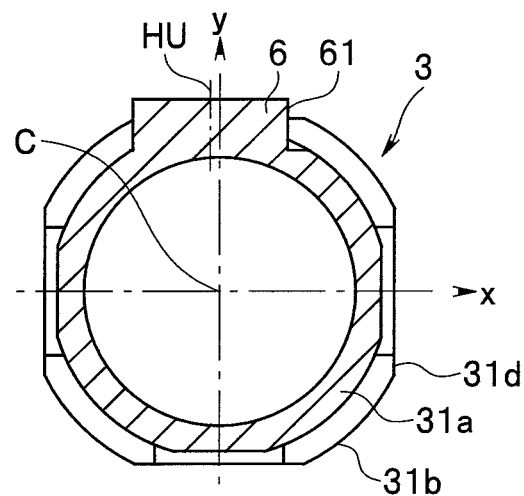
FIG. 37 is a sectional view of a movable section when viewed on a cut surface passing a XV-XV line shown in FIG. 38 in the fifth embodiment.
Figure 38:
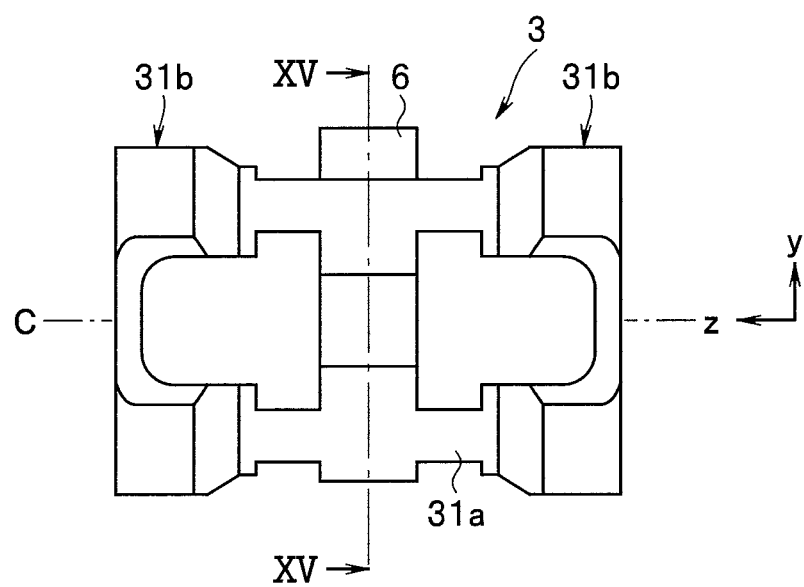
FIG. 38 is a side view showing a configuration of the movable section of the optical unit according to the fifth embodiment.

FIG. 34 to FIG. 38 show a fifth embodiment of the present invention. FIG. 34 is a sectional view of a configuration of an optical unit 1D when viewed on a cut surface perpendicular to the axis C. FIG. 35 is a sectional view of a fixed section main body 20D when viewed on a cut surface passing a XIV-XIV line shown in FIG. 36. FIG. 36 is a side view showing a configuration of the fixed section main body 20D of the optical unit 1D. FIG. 37 is a sectional view of the movable section 3 when viewed on a cut surface passing a XV-XV line shown in FIG. 38. FIG. 38 is a side view showing a configuration of the movable section 3 of the optical unit 1D.

In the fifth embodiment, explanation of the same portions as the portions in the first to fourth embodiments explained above is omitted as appropriate by, for example, denoting the portions with the same reference numerals and signs. Only differences are mainly explained.

In the embodiment, disposition of the thinned-down sections 21a in the fixed section main body 20D of a fixed section 2D is differentiated from the disposition in the first embodiment explained above.

In other words, as shown in FIGS. 34 to 36, among the four thinned-down sections 21a provided in a tube section 21D of the fixed section main body 20D, disposition of the thinned-down section 21a on the right side, the thinned-down section 21a on the upper side, and the thinned-down section 21a on the lower side is the same as the disposition in the first embodiment explained above. However, disposition of the thinned-down section 21a on the left side is different from the disposition in the first embodiment explained above.

More specifically, the center position HR around the axis C of the thinned-down section 21a on the right side in the x positive direction is present in a position further rotated slightly clockwise than the positive direction on the x axis. Therefore, in FIG. 36, the center position HR is located further on the lower side than the z-x plane. The center position HU around the axis C of the thinned-down section 21a on the upper side in the y positive direction is present in a position further rotated slightly counterclockwise than the positive direction on the y axis. Further, the center position HD around the axis C of the thinned-down section 21a on the lower side in the y negative direction is present in a position further rotated slightly counterclockwise than the negative direction on the y axis.

In contrast, the center position HL around the axis C of the thinned-down section 21a on the left side in the x negative direction is present in a position further rotated slightly counterclockwise than the negative direction on the x axis.

As shown in FIG. 36, both of the U-shaped cutout section 22d of an object-side thick section 22D and the U-shaped cutout section 23d of an image-side thick section 23D are disposed in circumferential direction positions corresponding to the thinned-down section 21a.

In this way, the embodiment is different from the first embodiment in that all of the four thinned-down sections 21a are disposed in positions deviating from the quadrisection positions around the axis C but a direction of the deviation from the quadrisection positions is different from the direction in the first embodiment.

As shown in FIG. 37 and FIG. 38, a configuration of the movable section 3 is the same as the configuration in the first embodiment explained above. Further, as shown in FIG. 34, a configuration of the voice coil motor 10 is also the same as the configuration in the first embodiment.

In the case of the embodiment, a direction of a resultant force F4 of the attraction forces F received by the magnet section 12, that is, the first magnet 12a and the second magnet 12b from the fixed section 2D is the radial direction of the movable section 3 as shown in FIG. 34. Although a rotational moment centering on the axis C is generated, since a part of the rotational moment is in an opposite direction and offset, it is possible to suppress rotation of the movable section 3 around the axis C.

According to such a fifth embodiment, although the configuration is different, it is possible to achieve substantially the same effects as the effects in the first embodiment explained above.

Further, according to the fifth embodiment, it is possible to gather, in one direction (the direction of the resultant force F4 of the attraction forces F), backlash due to sliding of the fixed section 2D and the movable section 3 and suppress a tilt of the movable section 3 around an axis orthogonal to the axis C and a shift of the movable section 3 in a direction parallel to the axis C.

Sixth Embodiment

Figure 39:
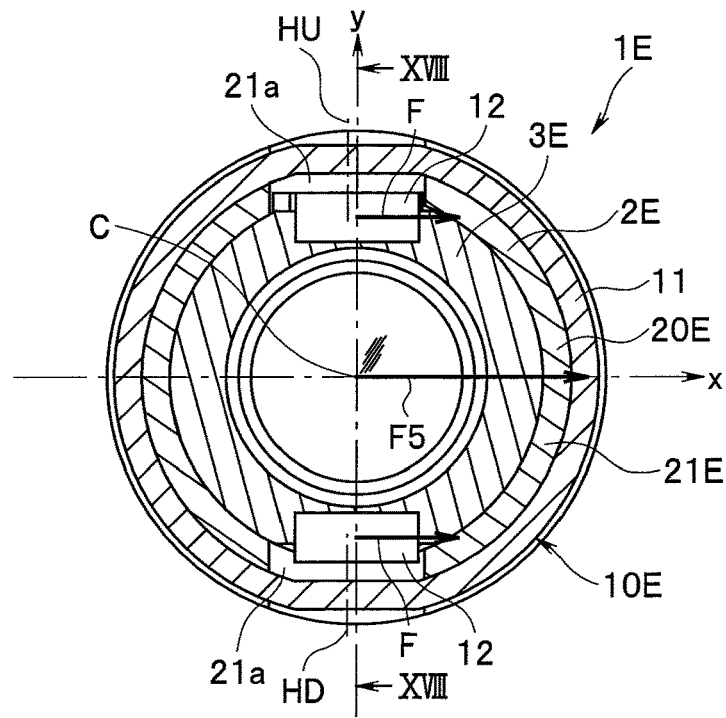
FIG. 39 is a sectional view of an optical unit when viewed on a cut surface passing a XVI-XVI line of FIG. 41 in a sixth embodiment of the present invention.
Figure 40:
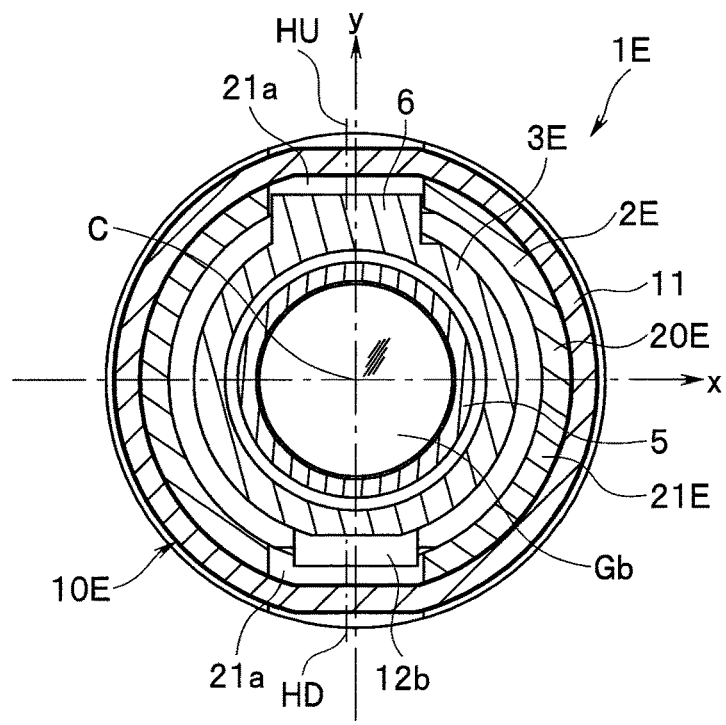
FIG. 40 is a sectional view of the optical unit when viewed on a cut surface passing a XVII-XVII line of FIG. 41 in the sixth embodiment.
Figure 41:
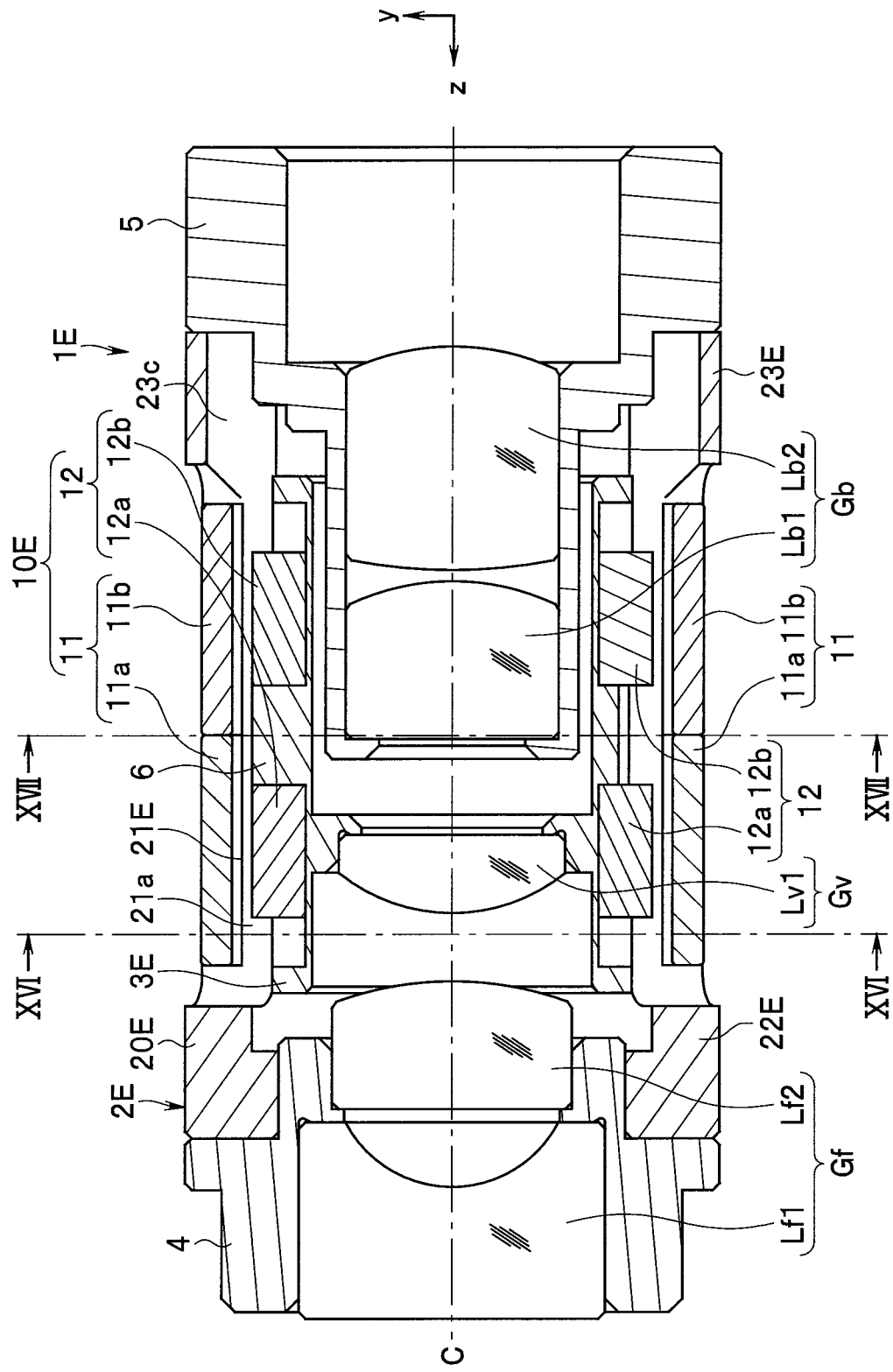
FIG. 41 is a sectional view of the optical unit when viewed on a cut surface passing a XVIII-XVIII line of FIG. 39 in the sixth embodiment.

FIG. 39 to FIG. 47 show a sixth embodiment of the present invention. FIG. 39 is a sectional view of an optical unit 1E when viewed on a cut surface passing a XVI-XVI line of FIG. 41. FIG. 40 is a sectional view of the optical unit 1E when viewed on a cut surface passing a XVII-XVII line of FIG. 41. FIG. 41 is a sectional view of the optical unit 1E when viewed on a cut surface passing a XVIII-XVIII line of FIG. 39.

In the sixth embodiment, explanation of the same portions as the portions in the first to fifth embodiments explained above is omitted as appropriate by, for example, denoting the portions with the same reference numerals and signs. Only differences are mainly explained.

In the voice coil motor 10 in the first to fifth embodiments explained above, n=4, where n represents the number of magnet sections 12, and the voice coil motor 10 includes the four magnet sections 12 in the quadrisection positions around the axis C. In the first to fifth embodiment, the four thinned-down sections 21a corresponding to the four magnet sections 12 are provided. In contrast, a voice coil motor 10E in the embodiment is different from the voice coil motor 10 in a configuration, and n=2. As shown in FIG. 39 to FIG. 41, the voice coil motor 10E includes two magnet sections 12 in bisection positions around the axis C. Two thinned-down sections 21a corresponding to the two magnet sections 12 are provided.

Figure 42:
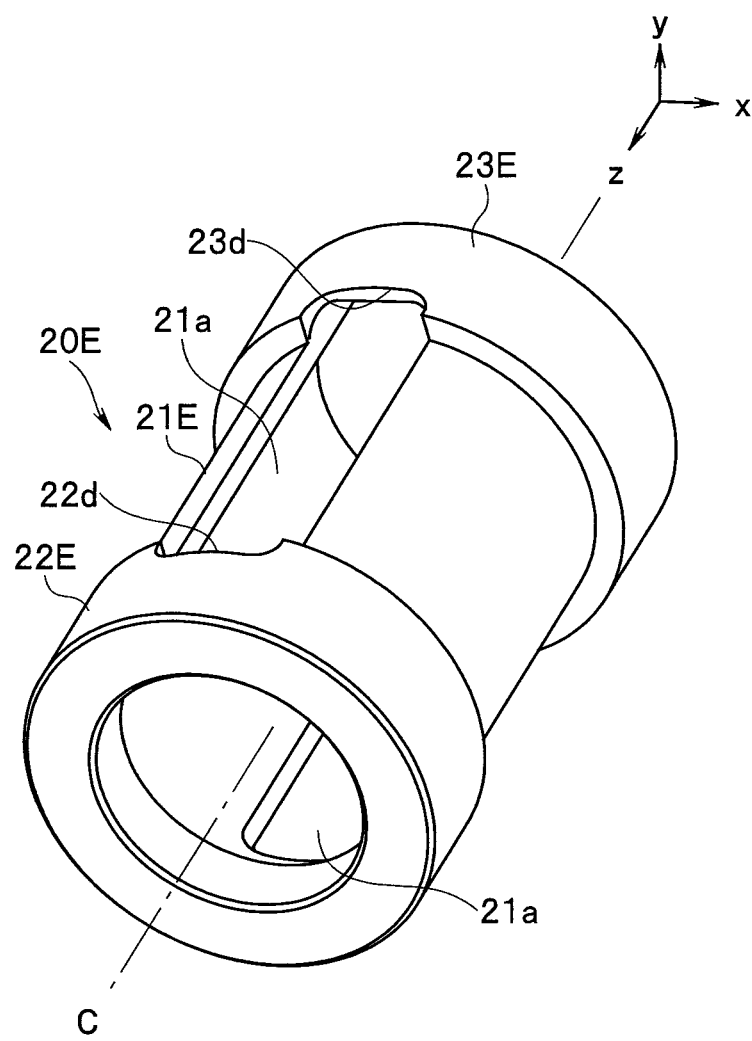
FIG. 42 is a perspective view showing a configuration of a fixed section main body of the optical unit according to the sixth embodiment.
Figure 43:
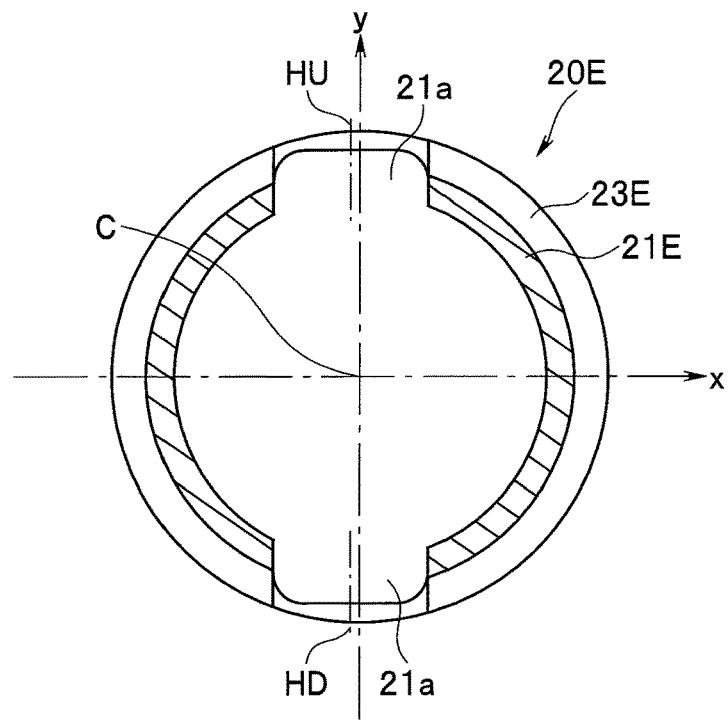
FIG. 43 is a sectional view of the fixed section main body when viewed on a cut surface passing a XIX-XIX line of FIG. 44 in the sixth embodiment.
Figure 44:
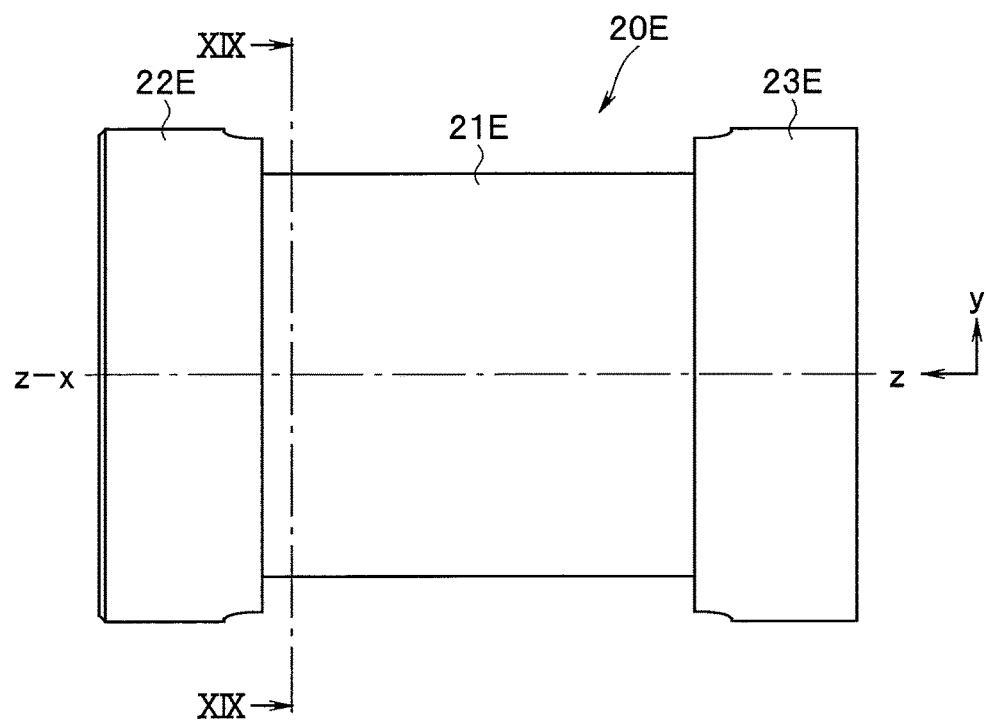
FIG. 44 is a side view showing a configuration of the fixed section main body of the optical unit according to the sixth embodiment.

FIG. 42 is a perspective view showing a configuration of a fixed section main body 20E of the optical unit 1E. FIG. 43 is a sectional view of the fixed section main body 20E when viewed on a cut surface passing a XIX-XIX line of FIG. 44. FIG. 44 is a side view showing a configuration of the fixed section main body 20E of the optical unit 1E.

As shown in FIG. 42 to FIG. 44, the fixed section main body 20E of a fixed section 2E includes a tube section 21E having the axis C as a center axis, a short tubular object-side thick section 22E formed on the object side in the axis C direction with respect to the tube section 21E, and a short tubular image-side thick section 23E formed on an opposite side of the object-side thick section 22E in the axis C direction with respect to the tube section 21E.

In the tube section 21E, two thinned-down sections 21a for housing the magnet sections 12 in a noncontact manner are disposed at substantially every 180° around the axis C. The two thinned-down sections 21a are disposed such that centers of the thinned-down sections 21a deviate from the bisection positions around the axis C.

More specifically, as shown in FIG. 39, FIG. 40, FIG. 43, and the like, the center position HU around the axis C of the thinned-down section 21a on the upper side in the y positive direction is present in a position further rotated slightly counterclockwise than the positive direction on the y axis. The center position HD around the axis C of the thinned-down section 21a on the lower side in the y negative direction is present in a position further rotated slightly clockwise than the negative direction on the y axis.

As shown in FIG. 41 and FIG. 42, both of the U-shaped cutout section 22d of the object-side thick section 22E and the U-shaped cutout section 23d and the groove 23c of the image-side thick section 23E are provided only in two parts on the upper side in the y positive direction and the lower side in the y negative direction.

Figure 45:
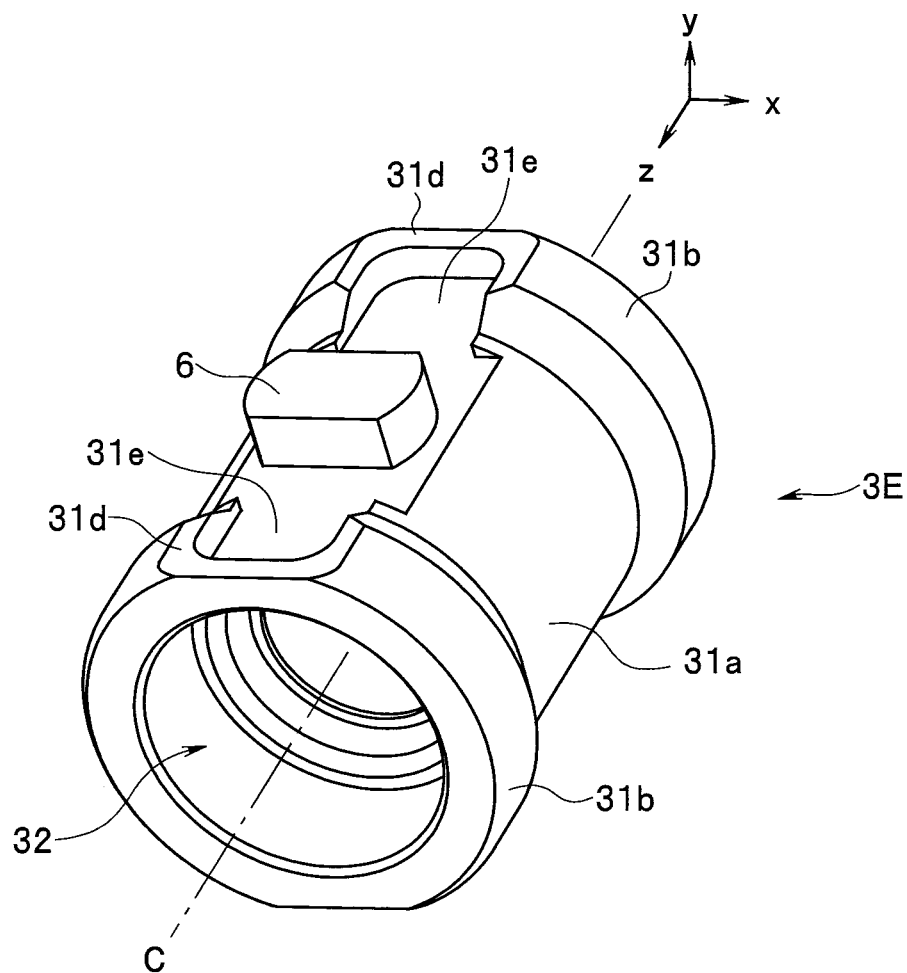
FIG. 45 is a perspective view showing a configuration of a movable section of the optical unit according to the sixth embodiment.
Figure 46:
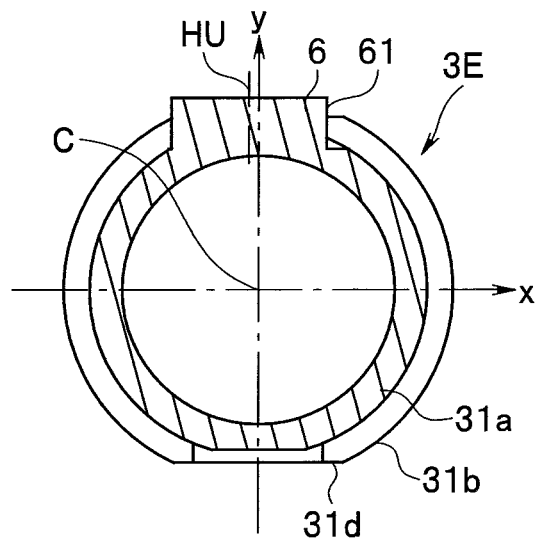
FIG. 46 is a sectional view of the movable section when viewed on a cut surface passing a XX-XX line of FIG. 47 in the sixth embodiment.
Figure 47:
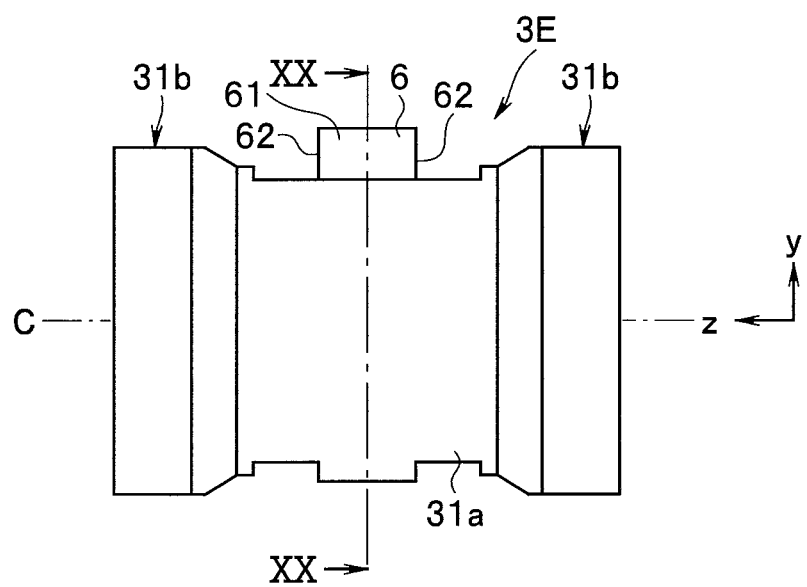
FIG. 47 is a side view showing the configuration of the movable section of the optical unit according to the sixth embodiment.

FIG. 45 is a perspective view showing a configuration of a movable section 3E of the optical unit 1E. FIG. 46 is a sectional view of the movable section 3E when viewed on a cut surface passing a XX-XX line of FIG. 47. FIG. 47 is a side view showing the configuration of the movable section 3E of the optical unit 1E.

As shown in FIG. 45 and FIG. 46, the plane sections 31d and the step sections 31e of the movable section 3E are also provided in only two parts on the upper side in the y positive direction and the lower side in the y negative direction. The rotation restricting section 6 is provided between one pair of the step sections 31e on the upper side in the y positive direction as in the first embodiment explained above.

The magnet sections 12 including the first magnets 12a and the second magnets 12b are respectively fixed to one pair of the step sections 31e on the upper side in the y positive direction and one pair of step sections 31e on the lower side in the y negative direction. The magnet sections 12 are disposed at every (360/2)°=180° in symmetrical positions around the axis C.

In the case of the embodiment, a direction of a resultant force F5 of the attraction forces F received by the magnet section 12, that is, the first magnet 12a and the second magnet 12b from the fixed section 2E is a radial direction of the movable section 3E as shown in FIG. 39. A rotational moment centering on the axis C is nearly zero.

According to such a sixth embodiment, even when n representing the number of magnet sections 12 is set to 2, since one pair of the thinned-down sections 21a is disposed in positions deviating from the bisection positions around the axis C, it is possible to achieve substantially the same effects as the effects in the first embodiment explained above.

According to the sixth embodiment, the number of magnet sections 12 is set smaller than the number of magnet sections 12 in the first to fifth embodiments explained above. Accordingly, it is possible to achieve a further reduction in the size and a further reduction in the weight of the optical unit.

Further, according to the sixth embodiment, it is possible to gather, in one direction (the direction of the resultant force F5 of the attraction forces F), backlash due to sliding of the fixed section 2E and the movable section 3E and suppress a tilt of the movable section 3E around an axis orthogonal to the axis C and a shift of the movable section 3E in a direction parallel to the axis C.

Seventh Embodiment

Figure 48:
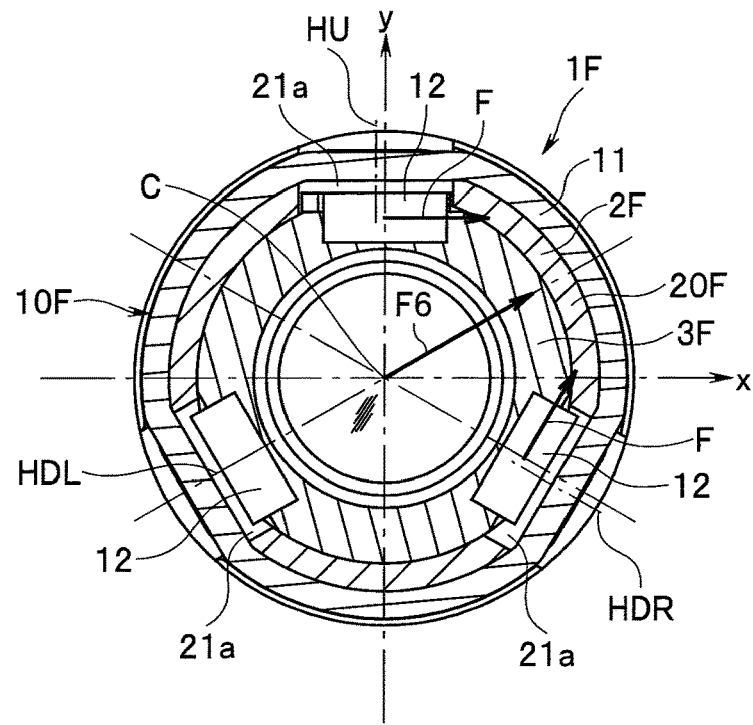
FIG. 48 is a sectional view of a configuration of an optical unit according to a seventh embodiment of the present invention when viewed on a cut surface perpendicular to the axis C.

FIG. 48 shows a seventh embodiment of the present invention. FIG. 48 is a sectional view of a configuration of an optical unit 1F when viewed on a cut surface perpendicular to the axis C.

In the seventh embodiment, explanation of the same portions as the portions in the first to sixth embodiments explained above is omitted as appropriate by, for example, denoting the portions with the same reference numerals and signs. Only differences are mainly explained.

A voice coil motor 10F in the embodiment is different from the voice coil motor 10 in a configuration and n representing the number of magnet sections 12 is 3.

In other words, three magnet sections 12 are provided in trisection positions around the axis C, that is, positions at every 120° on an outer circumferential side of a movable section 3F.

For example, it is assumed that angles are represented counterclockwise from the positive direction of the x axis. In a neutral position, a center of one magnet section 12 is disposed on the upper side of the y positive direction, that is, in a position of 90°. A center of another one magnet section 12 is disposed in a position of 210°. A center of still another one magnet section 12 is disposed in a position of 330°.

In a fixed section main body 20F of a fixed section 2F, three thinned-down sections 21a are provided in substantially trisection positions around the axis C corresponding to the three magnet sections 12.

The three thinned-down sections 21a are formed in asymmetrical positions deviating from the trisection positions around the axis C.

More specifically, the center position HU around the axis C of the thinned-down section 21a on the upper side in the y positive direction is present in a position further rotated slightly counterclockwise than the positive direction on the y axis. A center position HDR around the axis C of the thinned-down section 21a on the right lower side in the y negative direction and the x positive direction is present in a position further rotated slightly clockwise than the trisection position at 330°.

A center position HDL around the axis C of the thinned-down section 21a on the left lower side in the y negative direction and the x negative direction is present in the trisection position of 210°.

In the case of the embodiment, a direction of a resultant force F6 of the attraction forces F received by the magnet section 12, that is, the first magnet 12a and the second magnet 12b from the fixed section 2F is a radial direction of the movable section 3F. A rotational moment centering on the axis C is nearly zero.

According to such a seventh embodiment, since at least one pair of the thinned-down sections 21a is disposed in positions deviating from the trisection positions around the axis C, it is possible to achieve substantially the same effects as the effects in the first embodiment explained above.

Further, according to the seventh embodiment, it is possible to gather, in one direction (the direction of the resultant force F6 of the attraction forces F), backlash due to sliding of the fixed section 2F and the movable section 3F and suppress a tilt of the movable section 3F around an axis orthogonal to the axis C and a shift of the movable section 3F in a direction parallel to the axis C.

Eighth Embodiment

Figure 49:
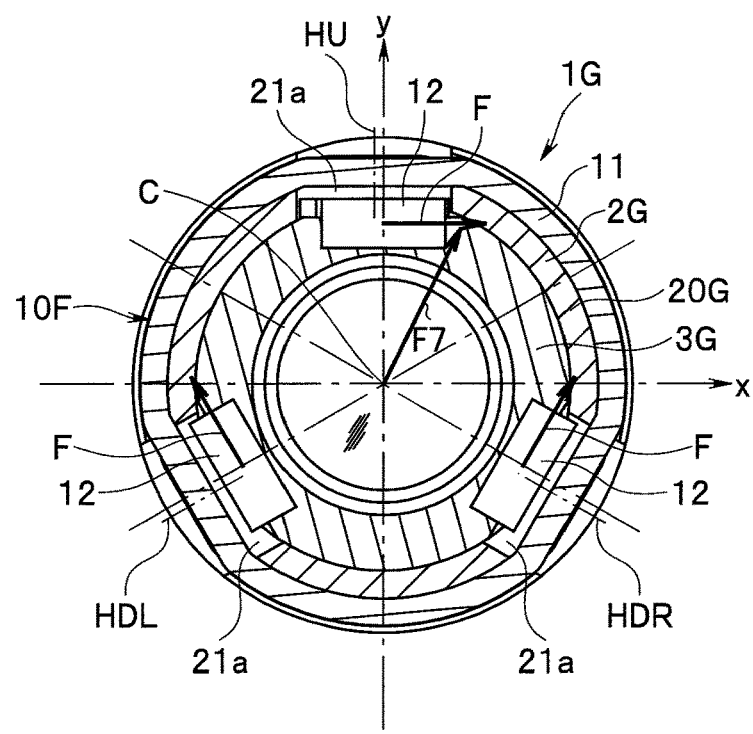
FIG. 49 is a sectional view of a configuration of an optical unit according to an eighth embodiment of the present invention when viewed on a cut surface perpendicular to the axis C.

FIG. 49 shows an eighth embodiment of the present invention. FIG. 49 is a sectional view of a configuration of an optical unit 1G when viewed on a cut surface perpendicular to the axis C.

In the eighth embodiment, explanation of the same portions as the portions in the first to seventh embodiments explained above is omitted as appropriate by, for example, denoting the portions with the same reference numerals and signs. Only differences are mainly explained.

Like the seventh embodiment explained above, the embodiment is also an embodiment in which the voice coil motor 10F, n representing the number of magnet sections 12 of which is 3, is used.

In other words, three magnet sections 12 are provided in trisection positions around the axis C on the outer circumference side of a movable section 3G, and disposition of the magnet sections 12 is the same as the disposition in the seventh embodiment explained above.

Three thinned-down sections 21a corresponding to the three magnet sections 12 are formed in asymmetrical positions deviating from the trisection positions around the axis C of a fixed section main body 20G in a fixed section 2G.

More specifically, the center position HU around the axis C of the thinned-down section 21a on the upper side in the y positive direction is present in a position further rotated slightly counterclockwise than the positive direction on the y axis. The center position HDL around the axis C of the thinned-down section 21a on the left lower side in the y negative direction and the x negative direction is present in a position further rotated slightly counterclockwise than the trisection position at 210°. The center position HDR around the axis C of the thinned-down section 21a on the right lower side in the y negative direction and the x positive direction is present in a position further rotated slightly clockwise than the trisection position at 330°.

In this way, disposition of the thinned-down sections 21a on the upper side and the right lower side is the same as the disposition in the seventh embodiment. However, disposition of the thinned-down section 21a on the left lower side is different from the disposition in the seventh embodiment and is disposition deviating from the trisection position.

In the case of the embodiment, a direction of a resultant force F7 of the attraction forces F received by the magnet section 12, that is, the first magnet 12a and the second magnet 12b from the fixed section 2G is a radial direction of the movable section 3G. Although a rotational moment centering on the axis C is generated, since a part of the rotational moment is in an opposite direction and offset, it is possible to suppress rotation of the movable section 3G around the axis C.

According to such an eighth embodiment, since at least one pair of the thinned-down sections 21a is disposed in positions deviating from the trisection positions around the axis C, it is possible to achieve substantially the same effects as the effects in the first embodiment explained above.

Further, according to the eighth embodiment, it is possible to gather, in one direction (the direction of the resultant force F7 of the attraction forces F), backlash due to sliding of the fixed section 2G and the movable section 3G and suppress a tilt of the movable section 3G around an axis orthogonal to the axis C and a shift of the movable section 3G in a direction parallel to the axis C.

Ninth Embodiment

Figure 50:
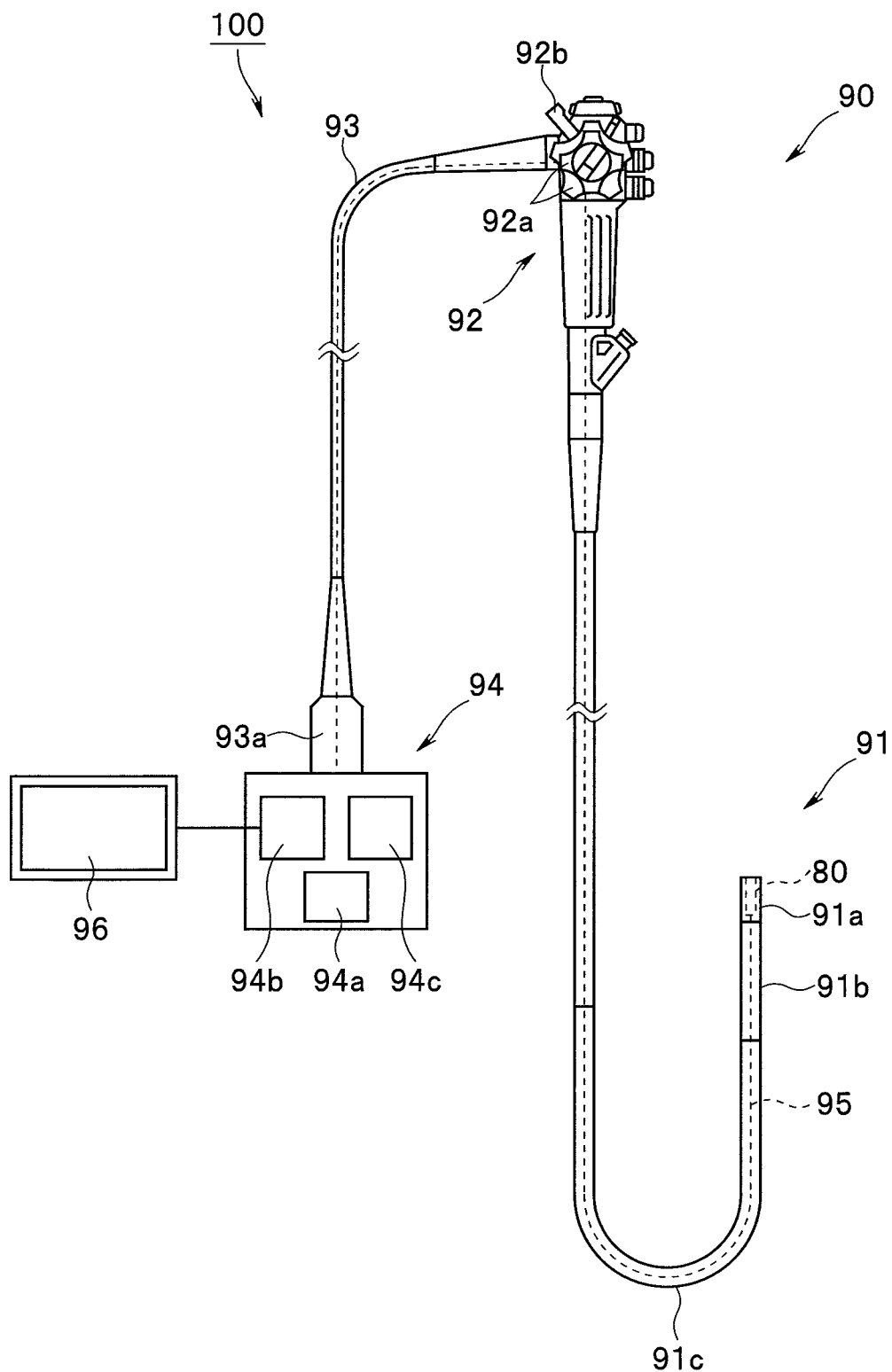
FIG. 50 is a diagram showing a configuration of an endoscope system including an endoscope including an optical unit according to a ninth embodiment of the present invention.

FIG. 50 shows a ninth embodiment of the present invention. FIG. 50 is a diagram showing a configuration of an endoscope system including an endoscope including an optical unit.

In the ninth embodiment, explanation of the same portions as the portions in the first to eighth embodiments explained above is omitted as appropriate by, for example, denoting the portions with the same reference numerals and signs. Only differences are mainly explained.

An endoscope system 100 shown in FIG. 50 includes an endoscope 90, a control apparatus 94, and a display apparatus 96.

The endoscope 90 is insertable into a subject such as a human body and optically observes a predetermined observation part in the subject. Note that the subject into which the endoscope 90 is inserted is not limited to the human body and may be another organism, may be an artificial object such as a machine or a building, or may be a natural object such as a cave. In other words, the endoscope 90 may be a medical endoscope, may be an industrial endoscope, or may be an endoscope used for, for example, science.

The endoscope 90 includes an insertion section 91 inserted into an inside of the subject, an operation section 92 located at a proximal end of the insertion section 91, and a universal cord 93 functioning as a composite cable extended from the operation section 92.

The insertion section 91 includes, in order from a distal end side toward the proximal end side, a distal end portion 91a, a bendable bending section 91b, and a flexible tube section 91c having flexibility. Note that a soft endoscope including the flexible tube section 91c is illustrated herein. However, the endoscope 90 may be a rigid endoscope not including the flexible tube section 91c in the insertion section 91. Further, the endoscope 90 may have a configuration in which the bending section 91b is omitted.

The endoscope 90 in the embodiment is configured as, for example, an electronic endoscope. An image pickup section 80 that condenses light from the subject and picks up a subject image is provided at the distal end portion 91a. However, the endoscope 90 may be configured as an optical endoscope.

More specifically, the image pickup section 80 includes an optical unit that condenses light from the subject and an image pickup device that photoelectrically converts the light condensed by the optical unit and outputs the light as an electric signal. As the optical unit, the optical unit 1 or 1A to 1G described in any one of the first to eighth embodiments can be applied.

The image pickup device is configured using, for example, a CCD (charge coupled device) or a CMOS (complementary metal oxide semiconductor).

The operation section 92 includes an angle operation section 92a and a zoom operation section 92b. The angle operation section 92a is a part that operates a bending state of the bending section 91b. The zoom operation section 92b is a part that operates a zoom operation in the optical unit to operate operation of the voice coil motor 10 (or the voice coil motor 10E or the voice coil motor 10F) explained above.

In an example shown in FIG. 50, the angle operation section 92a is formed in a knob shape and the zoom operation section 92b is formed in a lever shape. However, the angle operation section 92a and the zoom operation section 92b may each be formed as a volume switch, a push switch, or the like and are not limited to a specific operation system.

The universal cord 93 is a member that connects the operation section 92 and the control apparatus 94. The endoscope 90 is connected to the control apparatus 94 through a connector 93a provided at a proximal end portion of the universal cord 93.

A cable 95 including a wire, an electric wire, an optical fiber, and the like is inserted through the insertion section 91, the operation section 92, and the universal cord 93.

The wire is used for bending of the bending section 91b. The optical fiber is used for transmission of illumination light irradiated from the distal end portion 91a toward the subject. Further, the electric wire is used for transmission of electric power and a driving signal from the control apparatus 94 to the image pickup section 80, transmission of an image pickup signal, which is outputted from the image pickup device of the image pickup section 80, to the control apparatus 94, transmission of operation signals of the angle operation section 92a and the zoom operation section 92b to the control apparatus 94, and the like.

The control apparatus 94 includes a processor such as a CPU (central processing unit) and collectively controls the entire endoscope system 100. The control apparatus 94 includes a driving control section 94a, an image control section 94b, and a light-source control section 94c.

The driving control section 94a includes an actuator and is mechanically connected to the operation section 92 and the bending section 91b through the wire. The driving control section 94a receives an operation signal relating to angle operation and drives the actuator to advance and retract the wire to control the bending state of the bending section 91b.

The image control section 94b is electrically connected to the image pickup section 80 and the operation section 92 through the electric wire. The image control section 94b receives an operation signal relating to zoom operation and performs driving control of the voice coil motor 10 (or the voice coil motor 10E or the voice coil motor 10F) included in the image pickup section 80. Further, the image control section 94b controls to drive the image pickup device of the image pickup section 80 and performs image processing for an image pickup signal outputted from the image pickup section 80. An image processed by the image control section 94b in this way is displayed by the display apparatus 96.

The light-source control section 94c is connected to a not-shown light source apparatus separate from the control apparatus 94 or a light source apparatus provided on an inside of the control apparatus 94. The light-source control section 94c is optically connected to the light source apparatus and the operation section 92 through the optical fiber.

The light-source control section 94c controls brightness and the like of the illumination light irradiated from the distal end portion 91a toward the subject.

Note that, in the above explanation, the operation section 92 is formed integrally with the insertion section 91. However, the operation section 92 may be formed separately from the insertion section 91 and operation of the insertion section 91 may be performed by remote control. In the above explanation, an electric bending endoscope is explained as an example. However, the endoscope 90 may be a manual bending endoscope in which the wire is directly towed by the angle operation section 92a.

The endoscope system 100 configured as explained above includes the image pickup section 80 including the optical unit according to any one of the first to eighth embodiments. Accordingly, the endoscope system 100 can quickly perform a zoom change and is suitable for picking up a moving image. Since the optical unit is small in size, it is possible to reduce the distal end portion 91a in size and diameter and improve an insertion property. Further, since the length of a rigid portion in the distal end portion 91a can be reduced, bending operation is also easy.

In the optical unit according to any one of the first to eighth embodiments, since the magnet sections 12 are provided in the movable section and, on the other hand, the coil section 11 is provided in the fixed section, it is unnecessary to move the cable connected to the coil section 11. Accordingly, since the cable does not move in a limited space in the distal end portion 91a of the endoscope 90, disconnection of the cable does not occur and the endoscope system 100 is excellent in durability.

With such a ninth embodiment, substantially the same effects as the effects in the first to eighth embodiments explained above are achieved. The endoscope system 100 includes the endoscope 90 that includes the actuator reduced in size and weight and can perform quick advancing and retracting movement of the movable lens.

Other Embodiments

Note that the present invention is not limited to the configurations explained above. For example, at least one magnetic detector that detects magnetism and a current control section that controls, based on a detection result of the magnetic detector, an electric current flowing to the coil section 11 may be further included in the optical unit. The magnetic detector can be configured using, for example, a Hall element or a magneto-resistive effective element (MR element). The magnetic detector is fixed to a not-shown supporting member provided on a radial direction outer circumference side of the coil section 11. The current control section controls, based on the magnetism detected by the magnetic detector, an electric current flowing to the coil section 11. Consequently, it is possible to more accurately control driving speed and a stop position of the movable section.

The number n of magnet sections disposed in the movable section is not limited to the number n described in the first to eighth embodiments but is more preferably an even number as explained above.

The magnet sections and the rotation restricting section only have to be able to be assembled to the thinned-down sections provided in the fixed section. The thinned-down sections do not have to pierce through the fixed section to the radial direction outer circumference side as explained above.

Note that the present invention is not limited to the embodiments explained above per se. In an implementation stage, the constituent elements can be modified and embodied in a range not departing from the gist of the present invention. Forms of various inventions can be formed by appropriate combinations of a plurality of constituent elements disclosed in the embodiments. For example, several constituent elements may be deleted from all the constituent elements described in the embodiments. Further, the constituent elements described in different embodiments may be combined as appropriate. In this way, it goes without saying that various modifications and applications are possible within the range not departing from the gist of the invention.

What is claimed is:

1. An optical unit comprising:
   a movable section formed in a tubular shape for holding a movable lens group on an inner side;
   a fixed section formed in a tubular shape for holding, on an inner side, at least one of an object-side fixed lens group disposed further on an object side than the movable lens group and an image-side fixed lens group disposed further on an image side than the movable lens group, the fixed section being disposed on an outer side of the movable section to have a center axis common to the movable section; and
   a voice coil motor including n magnet sections disposed in the movable section, where n is an integer equal to or larger than 2, and a coil section disposed in the fixed section, the voice coil motor being able to move the movable section in a direction of the center axis relatively to the fixed section by applying an electric current to the coil section, wherein
   the n magnet sections are each magnetically polarized in a direction crossing the center axis and disposed at every $(360/n°)$ in symmetrical positions around the center axis in the movable section,
   the fixed section is formed in the tubular shape using a material having specific permeability larger than 1.0, n thinned-down sections for respectively housing the n magnet sections in a noncontact manner being provided in the fixed section, the n thinned-down sections each being one of a blind-hole or a through hole;
   the movable section includes a rotation restricting section disposed on an inside of at least one thinned-down section among the n thinned-down sections, and the rotation restricting section engages with the thinned-down section and restricts rotation of the movable section around the center axis to thereby maintain a state in which the n magnet sections are in noncontact with the fixed section, and
   the n thinned-down sections are formed in asymmetrical positions around the center axis and includes at least one pair of two thinned-down sections adjacent to each other around the center axis, an angle around the center axis of centers of the pair of thinned-down sections being different from the $(360/n)°$;
   wherein each of the n magnet sections having a same size.

2. The optical unit according to claim 1, wherein the coil section is configured by winding a magnet wire around the center axis.

3. The optical unit according to claim 2, wherein
   each of the magnet sections includes a first magnet disposed on the object side and a second magnet disposed on the image side in a direction of the center axis, magnetic polarization directions of the first magnet and the second magnet are opposite to each other, and one of the first magnet and the second magnet has a component in an outer diameter direction centering on the center axis and another of the first magnet and the second magnet has a component in an inner diameter direction centering on the center axis, the coil section includes a first coil opposed to each of the first magnet of the n magnet sections and a second coil opposed to each of the second magnet of the n magnet sections and connected to the first coil, and in the first coil and the second coil, directions in which an electric current rotates and flows around the center axis are opposite.

4. The optical unit according to claim 3, wherein the rotation restricting section is disposed between the first magnet and the second magnet of at least one of the magnet sections.

5. The optical unit according to claim 1, wherein an angle range of the rotation restricting section centering on the center axis is larger than an angle range of one of the magnet sections.

6. The optical unit according to claim 1, wherein, in the rotation restricting section, at least a portion in contact with the fixed section is formed with a rounded shape.

7. The optical unit according to claim 1, wherein the number n of the magnet sections is an even number.

8. An endoscope that is inserted into an inside of a subject and observes the inside of the subject, the endoscope comprising:

the optical unit according to claim 1; and an image pickup device configured to convert light condensed by the optical unit into an electric signal.

9. The optical unit according to claim 1, wherein each of the n thinned-down sections having a same size.

* * * * *